US012734266B2

(12) United States Patent
Kim et al.

(10) Patent No.: US 12,734,266 B2
(45) Date of Patent: Sep. 15, 2026

(54) PHOTOCATALYST FILTER AND ELECTRONIC DEVICE COMPRISING SAME

(71) Applicant: SAMSUNG ELECTRONICS CO., LTD., Suwon-si (KR)

(72) Inventors: Sungwon Kim, Suwon-si (KR); Jeeyeon Kim, Suwon-si (KR); Heejin Park, Suwon-si (KR); Saemi Kim, Suwon-si (KR); Joonho Kim, Suwon-si (KR); Soomin Park, Suwon-si (KR); Yongwon Jeong, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 585 days.

(21) Appl. No.: 18/123,686

(22) Filed: Mar. 20, 2023

(65) Prior Publication Data

US 2023/0226248 A1 Jul. 20, 2023

Related U.S. Application Data

(63) Continuation of application No. PCT/KR2021/012770, filed on Sep. 17, 2021.

(30) Foreign Application Priority Data

Sep. 18, 2020 (KR) ........................ 10-2020-0120891

(51) Int. Cl.
*A61L 9/20* (2006.01)
*A61L 9/014* (2006.01)
(Continued)

(52) U.S. Cl.
CPC ............... *A61L 9/205* (2013.01); *A61L 9/014* (2013.01); *B01D 53/007* (2013.01);
(Continued)

(58) Field of Classification Search
CPC ....... A61L 9/014; A61L 9/205; B01D 53/007; B01D 53/0446; B01D 53/0454; B01D 53/8696; B01D 53/885
See application file for complete search history.

(56) References Cited

U.S. PATENT DOCUMENTS

2004/0146437 A1 7/2004 Arts et al.
2006/0096459 A1 5/2006 Iwano et al.
(Continued)

FOREIGN PATENT DOCUMENTS

CN 109210635 A 1/2019
CN 109844411 A 6/2019
(Continued)

OTHER PUBLICATIONS

Machine translation of WO201721497 (Year: 2017).*
(Continued)

*Primary Examiner* — Timothy C Cleveland
(74) *Attorney, Agent, or Firm* — Sughrue Mion, PLLC

(57) ABSTRACT

An electronic device includes a housing, a photocatalyst filter, at least one first sensor provided in the housing, a blower fan configured to introduce air into the housing, a light source configured to emit light to the photocatalyst filter, and a processor configured to control the blower fan and the light source, determine a degree of contamination of the photocatalyst filter based on a difference in sensor values between the at least one first sensor provided in the housing and at least one second sensor outside of the housing or a rate of change in sensor values between the at least one first sensor provided in the housing and the at least one second sensor outside the housing, and recycle the photocatalyst filter based on the determined degree of contamination of the photocatalyst filter.

15 Claims, 18 Drawing Sheets

(51) Int. Cl.

| | |
|---|---|
| ***B01D 53/00*** | (2006.01) |
| ***B01D 53/04*** | (2006.01) |
| ***B01D 53/86*** | (2006.01) |
| ***B01D 53/88*** | (2006.01) |
| ***F24F 8/167*** | (2021.01) |
| ***F24F 8/80*** | (2021.01) |

(52) U.S. Cl.

CPC ..... *B01D 53/0446* (2013.01); *B01D 53/0454* (2013.01); *B01D 53/8696* (2013.01); *B01D 53/885* (2013.01); *F24F 8/167* (2021.01); *F24F 8/80* (2021.01); *A61L 2209/111* (2013.01); *A61L 2209/12* (2013.01); *A61L 2209/14* (2013.01); *A61L 2209/22* (2013.01); *B01D 2255/802* (2013.01); *B01D 2257/302* (2013.01); *B01D 2257/304* (2013.01); *B01D 2257/404* (2013.01); *B01D 2257/406* (2013.01); *B01D 2257/708* (2013.01); *B01D 2257/91* (2013.01); *B01D 2259/40083* (2013.01)

(56) References Cited

U.S. PATENT DOCUMENTS

| | | | |
|---|---|---|---|
| 2010/0196223 | A1 | 8/2010 | Hay et al. |
| 2018/0104374 | A1 | 4/2018 | Kim et al. |
| 2018/0207311 | A1 | 7/2018 | Cho et al. |

FOREIGN PATENT DOCUMENTS

| | | | | | |
|---|---|---|---|---|---|
| CN | 211302674 | U | | 8/2020 | |
| DE | 102016209952 | A1 | | 12/2017 | |
| EP | 0798143 | A1 | | 10/1997 | |
| EP | 3 306 218 | A1 | | 4/2018 | |
| JP | 5-223312 | A | | 8/1993 | |
| JP | 8-243432 | A | | 9/1996 | |
| JP | 9-309329 | A | | 12/1997 | |
| JP | 10-33653 | A | | 2/1998 | |
| JP | 10-227469 | A | | 8/1998 | |
| JP | 2001-187122 | A | | 7/2001 | |
| JP | 2001-238939 | A | | 9/2001 | |
| JP | 2006-98037 | A | | 4/2006 | |
| JP | 2009-192126 | A | | 8/2009 | |
| JP | 2011-158203 | A | | 8/2011 | |
| JP | WO2019/193825 | A1 | | 4/2020 | |
| KR | 20-0164637 | | | 2/2000 | |
| KR | 10-0778669 | B1 | | 11/2007 | |
| KR | 10-2010-0001396 | A | | 1/2010 | |
| KR | 10-2016-0061867 | A | | 6/2016 | |
| KR | 10-2017-0115750 | A | | 10/2017 | |
| KR | 10-1825033 | B1 | | 2/2018 | |
| KR | 10-1837861 | B1 | | 3/2018 | |
| KR | 10-2018-0043163 | A | | 4/2018 | |
| KR | 10-1971456 | B1 | | 8/2019 | |
| WO | WO-2017211497 | A1 | * | 12/2017 | ......... B01D 53/8625 |

OTHER PUBLICATIONS

Communication dated Feb. 7, 2024 issued by the European Patent Office in European Patent Application No. 21869774.

International Search Report (PCT/ISA/210) issued Dec. 21, 2021 by the International Searching Authority in International Application No. PCT/KR2021/012770.

Written Opinion (PCT/ISA/237) issued Dec. 21, 2021 by the International Searching Authority in International Application No. PCT/KR2021/012770.

Communication issued Feb. 13, 2025 by the Korean Intellectual Property Office in Korean Patent Application No. 10-2020-0120891.

Communication issued Jan. 20, 2026 by the China National Intellectual Property Administration in Chinese Patent Application No. 202180064312.7.

Communication dated Jun. 1, 2026, issued by the China National Intellectual Property Administration in Chinese Application No. 202180064312.7.

* cited by examiner

PHOTOCATALYST FILTER AND ELECTRONIC DEVICE COMPRISING SAME

CROSS-REFERENCE TO RELATED APPLICATION(S)

This application is a bypass continuation of International Application No. PCT/KR2021/012770, filed on Sep. 17, 2021, in the Korean Intellectual Property Receiving Office, which is based on and claims priority to Korean Patent Application No. 10-2020-0120891, filed on Sep. 18, 2020, in the Korean Intellectual Property Office, the disclosures of which are incorporated herein by reference in their entireties.

BACKGROUND

1. Field

The disclosure relates to a photocatalyst filter and an electronic device including the same.

2. Description of Related Art

Maintaining hygiene and cleanliness in indoor spaces has become more important due to factors such as degradation of the atmospheric environment due to high concentration of fine dust and/or yellow dust, infectious diseases including bacteria and viruses, etc.

Accordingly, as the demand for air purification devices (e.g., air purifiers) for purifying indoor air increases, various types of air purification devices have been launched.

In the indoor space, volatile organic compounds (VOCs) generated from furniture, decoration and building materials may present various issues. Volatile organic compounds may degrade indoor environment quality and cause health issues, such as headaches, allergies, and nausea.

To remove these volatile organic compounds, an air purification devices including an adsorption deodorizing filter containing activated carbon have been utilized.

However, the adsorbent deodorizing filter suffers from poor durability and odor generation due to desorption of adsorbed odor gas and proliferation of adsorbed harmful microorganisms.

Related art purification devices including a filter using photocatalytic degradation (hereinafter referred to as 'photocatalyst filter') have been implemented to address the above limitations.

The photocatalyst filter may completely decompose volatile organic compounds (VOCs) into carbon dioxide and water, which are harmless to the human body, and may also be effective in removing bacteria or microorganisms when ultraviolet (UV) light is used. For example, as the photocatalyst filter, a photocatalyst filter including a photocatalyst material, (e.g., titanium dioxide (TiO2)), may be used. Titanium dioxide generates radicals (e.g., OH) when exposed to UV rays. The strong oxidizing power of these radicals may sterilize microorganisms and decompose odor-causing substances.

The photocatalyst material may decompose pollutants adsorbed in the filter, using a light source, so that it may be used semi-permanently. Therefore, it also benefits the user in terms of reduction in maintenance cost due to filter replacement and ease of management.

To use a photocatalyst filter containing a photocatalyst material, a light source, such as a light-emitting diode (LED), should be provided in the air purification device. As more light sources are provided, the air purifying effect may increase, but manufacturing costs and energy consumption rise accordingly.

Further, blind spots which are not reached by the light emitted from the light source may be formed near the edge or back surface of the photocatalyst filter. In the blind spots, air contaminants remain, causing deterioration of the air purifying effect.

SUMMARY

Provided are a photocatalyst filter capable of enhancing the air purifying effect while saving energy consumption and an electronic device including the same.

Further, provided are a photocatalyst filter to increase the recycling efficiency of the photocatalyst filter and air purifying effect by preventing contaminants from remaining in blind spots and an electronic device including the same.

Additional aspects will be set forth in part in the description which follows and, in part, will be apparent from the description, or may be learned by practice of the presented embodiments.

According to an aspect of the disclosure, an electronic device may include a housing, a photocatalyst filter, at least one first sensor provided in the housing, a blower fan configured to introduce air into the housing, a light source configured to emit light to the photocatalyst filter, and a processor configured to control the blower fan and the light source, determine a degree of contamination of the photocatalyst filter based on a difference in sensor values between the at least one first sensor provided in the housing and at least one second sensor outside of the housing or a rate of change in sensor values between the at least one first sensor provided in the housing and the at least one second sensor outside the housing, and recycle the photocatalyst filter based on the determined degree of contamination of the photocatalyst filter.

The photocatalyst filter may include a body including an internal space through which a fluid passes, a plurality of photocatalyst beads provided in the internal space, and a flap assembly connected with the body and configured to open or close based on a flow of the fluid, where a reflecting plate is provided on one surface of the flap assembly and is configured increase an amount of light reaching the plurality of photocatalyst beads by reflecting light when the flap assembly is closed.

The body may include a first opening provided on a front surface of the body and a second opening provided on a rear surface of the body, the flap assembly may be further configured to open or close over the second opening, and the reflecting plate may be provided on one surface of the flap assembly and is configured to face the first opening when the flap assembly is closed over the second opening.

The flap assembly may include a passive flap assembly configured to be opened or closed by the air introduced into the housing by the blower fan.

The plurality of photocatalyst beads may include hybrid beads, and the hybrid beads may include a photocatalyst material that decomposes at least some of contaminants in the fluid by causing photocatalytic oxidation, and an adsorbent that absorbs at least some of the contaminants in the fluid.

The reflecting plate may include a light scattering material or a portion provided on a surface thereof and that is configured to scatter light.

The housing may include a flap assembly configured to open or close based on a flow of a fluid, the photocatalyst filter may include a plurality of photocatalyst beads, and a reflecting plate may be provided on one surface of the flap assembly and may be configured to increase an amount of light reaching the plurality of photocatalyst beads when the flap assembly is closed.

The processor may be further configured to, after an air clean mode of the electronic device is terminated, recycle the photocatalyst filter based on an amount of increase of a first sensor value obtained by the at least one first sensor provided in the housing being larger than an amount of increase of a second sensor value obtained from the at least one second sensor outside the housing.

The processor may be further configured to, while an air clean mode of the electronic device is running, recycle the photocatalyst filter based on an amount of decrease of a first sensor value obtained by the at least one first sensor provided in the housing being smaller than an amount of decrease of a second sensor value obtained from the at least one second sensor outside the housing.

The photocatalyst filter may be recycled based on a determination of a recycling time by the processor.

The processor may be further configured to increase an amount of light emitted by the light source in a recycling mode of the photocatalyst filter.

The processor may be further configured to increase an intensity of light emitted by the light source in a recycling mode of the photocatalyst filter.

The processor may be further configured to change a light radiation direction of the light source in a recycling mode of the photocatalyst filter.

The processor may be further configured to reverse an air flow direction of the blower fan in a recycling mode of the photocatalyst filter.

The photocatalyst filter may include a plurality of subfilters which are separated, and a front section of the plurality of subfilters and a rear section of the plurality of subfilters may be switched in a recycling mode of the photocatalyst filter.

According to an aspect of the disclosure, a photocatalyst filter may include a body including an internal space through which a fluid passes, a plurality of photocatalyst beads provided in the internal space, a flap assembly connected to the body and configured to open or close based on a flow of the fluid, and a reflecting plate provided on a surface of the flap assembly, the reflecting plate configured to increase an amount of light reaching the plurality of photocatalyst beads when the flap assembly is closed.

The body may include a first opening provided on a front surface of the body and a second opening provided on a rear surface of the body, the flap assembly may be further configured to open or close over the second opening, and the reflecting plate may be configured to face the first opening when the flap assembly is closed over the second opening.

The plurality of photocatalyst beads may include hybrid beads and the hybrid beads may include a photocatalyst material that decomposes at least some of contaminants in the fluid by causing photocatalytic oxidation and an adsorbent that absorbs at least some of the contaminants in the fluid.

The photocatalyst filter further may include a plurality of subfilters which are separated, and a front section of the plurality of subfilters and a rear section of the plurality of subfilters may be switched in a recycling mode of the photocatalyst filter.

According to an aspect of the disclosure, a method may include obtaining at least one first sensor value from at least one first sensor provided in a housing of an electronic device including a photocatalyst filter, obtaining at least one second sensor value from at least one second sensor outside of the housing of the electronic device, determining a degree of contamination of the photocatalyst filter based on a difference between the at least one first sensor value and the at least one second sensor value or a rate of change in sensor values between the at least one first sensor value and the at least one second sensor value, and recycling the photocatalyst filter based on the determined degree of contamination in the photocatalyst filter.

BRIEF DESCRIPTION OF DRAWINGS

The above and other aspects, features, and advantages of certain embodiments of the present disclosure will be more apparent from the following description taken in conjunction with the accompanying drawings, in which.

DETAILED DESCRIPTION

Various embodiments of the disclosure are described and shown to thoroughly explain the disclosure to those skilled in the art, and various modifications may be made thereto, and the scope of the present disclosure is not limited thereto. Embodiments of the disclosure are provided to fully and thoroughly convey aspects of the disclosure to those skilled in the art.

As used herein, the thickness and size of each layer may be exaggerated or shrunken for ease or clarity of description. The same reference denotations may be used to refer to the same or substantially the same elements throughout the specification and the drawings. As used herein, the term "A and/or B" encompasses any, or one or more combinations, of A and B.

Figure 1:
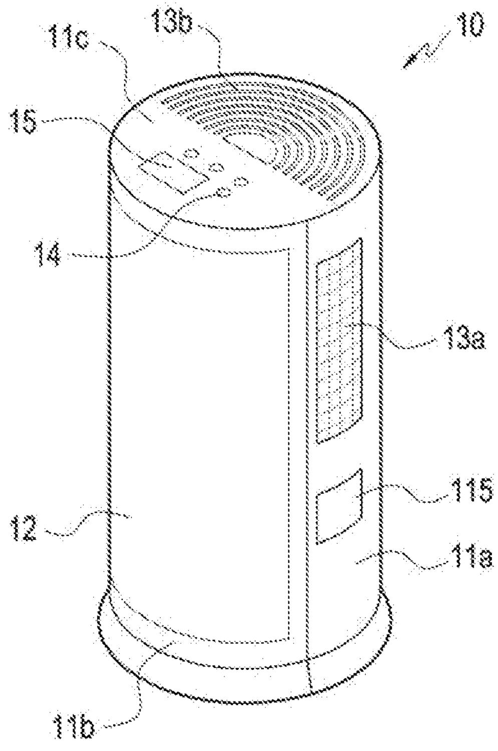
FIG. 1 is a diagram illustrating an electronic device according to various embodiments of the disclosure.

FIG. 1 is a diagram illustrating an electronic device according to various embodiments of the disclosure.

According to various embodiments of the disclosure, the electronic device 10 may correspond to an air purification device (or an air conditioner). The air purification device may refer to any device installed in a home or office to purify the air. The air purification device may be a device incorporating a blower used to collect dust floating in the air or remove gas. The air purification device may be a device for adjusting the temperature and humidity of indoor air. For example, the air purification device may be implemented as an air purifier, an air conditioner, or a humidifier. Alternatively, the air purification device may be implemented as an air purification component provided in a refrigerator, a kimchi refrigerator, a washing machine, a dryer, a clothing care device, a shoe closet, a closet, a septic tank, an air conditioning system, and the like. The air purification device may encompass examples of various devices for the purpose of purifying and deodorizing indoor air.

The electronic device 10 may include a housing 11 that forms a space inside and forms the outer appearance, an inlet 12 that is formed on one side of the housing 11 to intake air, outlets 13*a* and 13*b* that discharge the air introduced into the inside of the housing 11, an input unit 14 for inputting user commands, and display units 15 and 115 for displaying the operation state of the electronic device 10.

The housing 11 may include a main body 11*a*, a front cover 11*b* couplable to the main body 11*a*, and an upper cover 11*c*. Some of the aforementioned components may be omitted, or one or more other components may be further added to the housing 11. FIG. 1 illustrates a configuration in which the main body 11*a* is separated from the front cover 11*b* and the upper cover 11*c*, but may be integrally formed otherwise. Other various embodiments may also be applicable.

The number and position of the inlet 12 and the outlet 13*a* and 13*b* are not limited to any particular embodiment. FIG. 1 illustrates that the inlet 12 is formed in the front cover 11*b* of the housing 11, and the first and second outlets 13*a* and 13*b* are formed in the front cover 11*b* and the upper cover 11*c*, respectively. However, embodiments are not limited thereto.

The input unit 14 may include a power button for turning on or off the electronic device 10, a timer button for setting a driving time of the electronic device 10, and a lock button for limiting the manipulation of the input unit to prevent wrong manipulation of the input unit. There may further be included a button for inputting various control information for the electronic device 10. In this case, the input unit 14 may adopt a push switch type in which an input signal is generated by the user's pressing or a touch switch type in which an input signal is generated through the user's touch on her body portion. If the input unit 14 adopts the touch switch type, the input unit 14 may be integrally implemented with the display unit 15.

The display units 15 and 115 may display information about the state of the electronic device 10. For example, the display units may display information about the degree of contamination of the photocatalyst filter (e.g., photocatalyst filter 240), information about the replacement time of the photocatalyst filter 240, information about the filling rate of beads (e.g., beads 300) in the photocatalyst filter (e.g., information about the filled number, filling ratio at each time, or whether filling is required), information about the state of the photocatalyst filter (e.g., information about days used after filled with photocatalyst beads or accrued time), information about the activity currently in progress (e.g., information about whether it is the air quality sensing step or filtering step and information about the air flow direction). The information may be provided per multiple spaces in the photocatalyst filter. Such information may be provided through the display units 15 and 115 and, according to another embodiment, be provided from an external device (e.g., a smartphone communicating with the electronic device 10). The display units 15 and 115 may be disposed in any positions on the housing 11 where it may easily be viewed by the user. In FIG. 1, as the display units 15 and 115, the display unit 15 is disposed on the upper cover 11*c*, and the display unit 115 is disposed on the main body 11*a*, but such embodiment is not limited. According to an embodiment, a user interface (UI) including the above-described information may be displayed on the display unit 15 of the electronic device 10 or on an external device.

Figure 2:
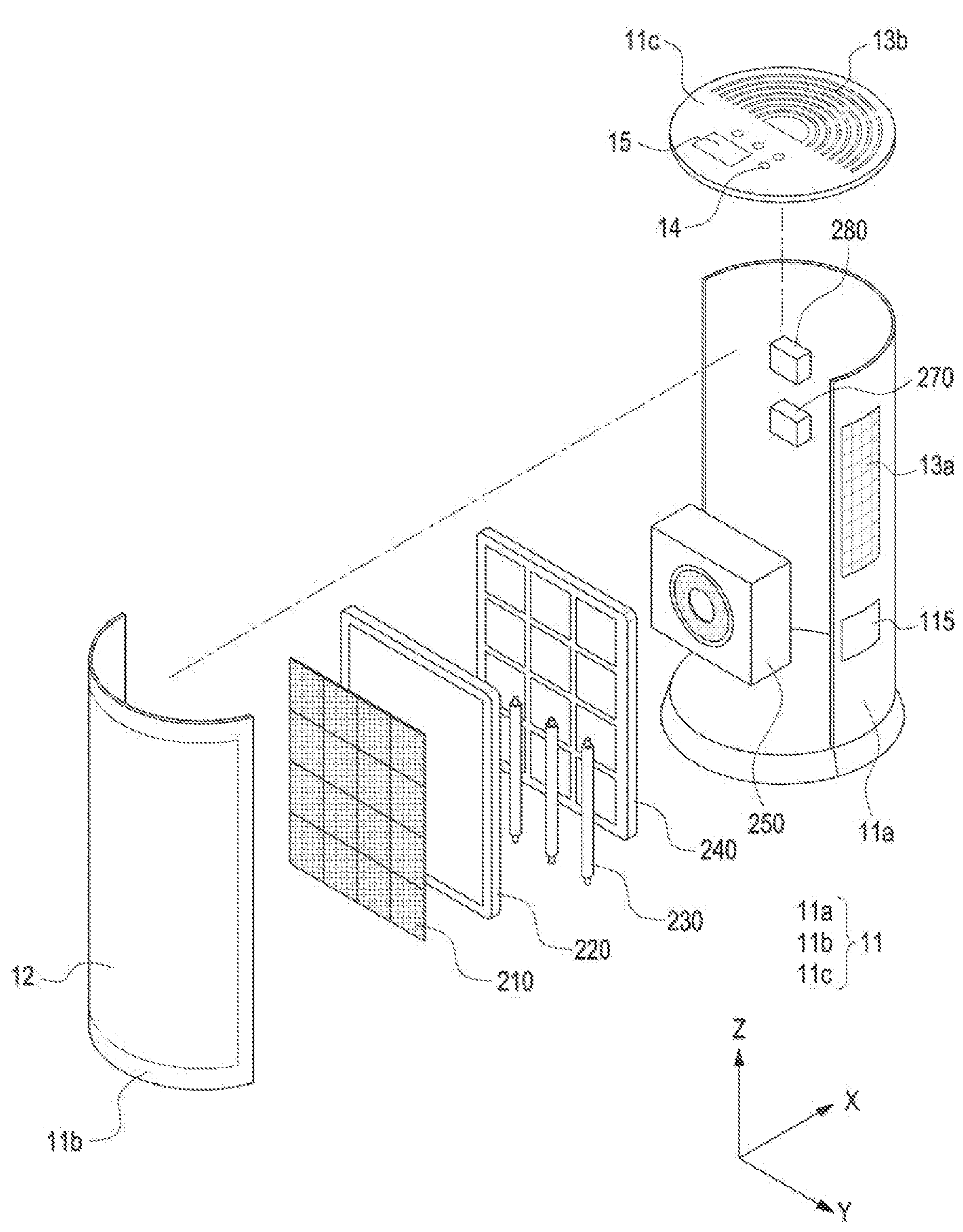
FIG. 2 is a diagram illustrating an electronic device according to various embodiments of the disclosure.
Figure 3:
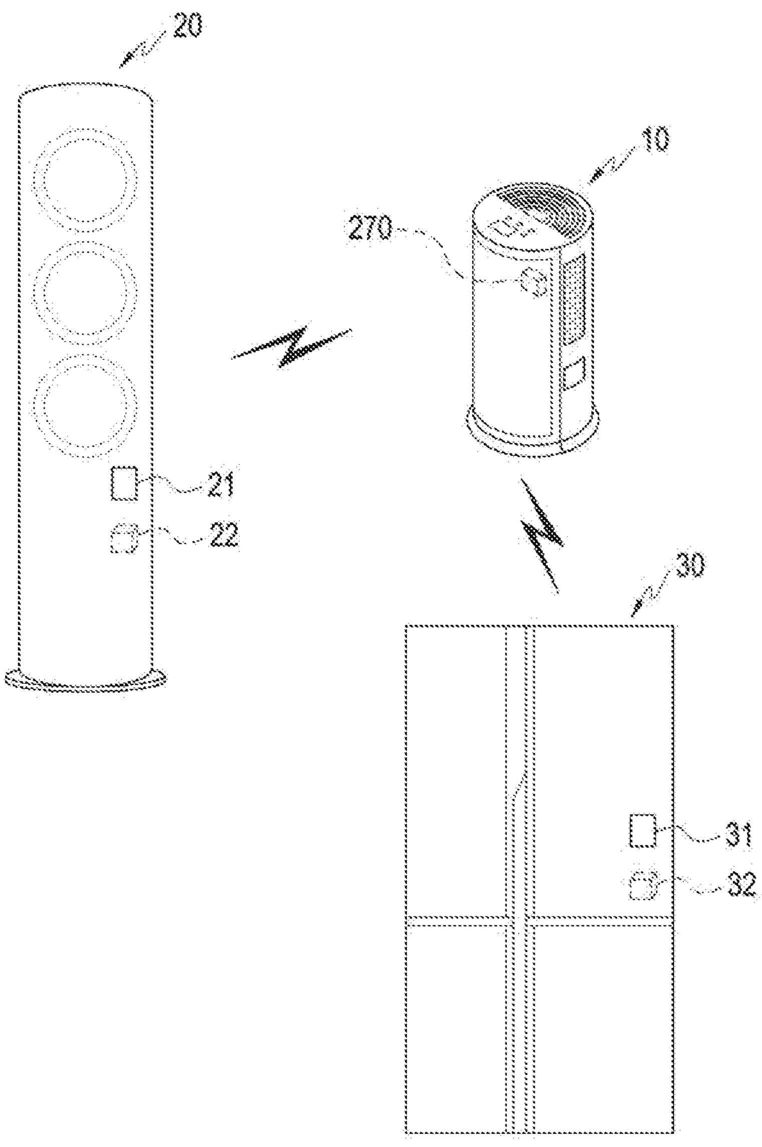
FIG. 3 is a diagram illustrating an electronic device and an external electronic device according to various embodiments of the disclosure.

FIG. 2 is a diagram illustrating an electronic device 10 according to various embodiments of the disclosure. FIG. 3 is a diagram illustrating an electronic device 10 and external electronic devices 20 and 30 according to various embodiments of the disclosure.

The electronic device 10 may include a pre-filter 210, a high-efficiency particulate absorbing (HEPA) filter 220, a light source 230, a photocatalyst filter 240, and a blower fan 250. Further, the electronic device 10 may include a controller or processor 280 for performing the operation for driving the blower fan 250, radiation from the light source 230, and recycling of the photocatalyst filter 240 and may include a first sensor 270 for detecting the air quality inside the electronic device 10.

The pre-filter 210 may be a component for filtering out relatively large dust particles and may be disposed closest to the inlet 12. The HEPA filter 220 may be a component disposed behind the pre-filter 210 to filter (e.g., fine dust which is not filtered by the pre-filter 210). The pre-filter 210 may primarily filter dust, and the HEPA filter 220 having relatively higher performance than the pre-filter 210 may secondarily filter dust. Here, the HEPA filter 220 may be formed of, for example, a glass fiber. A deodorizing filter including activated carbon may be further included between the pre-filter 210 and the HEPA filter 220 or behind the HEPA filter 220. The filters may be arranged in the order shown in FIG. 2 or may be arranged in a different order. Alternatively, it is also possible to omit any one of the filters 210 and 220.

The light source 230 may be a component for radiating light toward the photocatalyst filter 240. The photocatalyst material of the photocatalyst filter 240 may react with light emitted from the light source 230 to remove harmful gases, odor substances, microorganisms, etc. The light source 230 may emit light suitable for causing a photocatalyst reaction in the photocatalyst material included in the photocatalyst filter 240. For example, the light source 230 may be implemented as a device, such as a fluorescent lamp or an incandescent lamp or a light-emitting diode (LED), and it may emit at least one type of light among white light, red light, green light, blue light, ultraviolet light, visible light, or infrared light. For example, the light source 230 may be provided as an assembly with a lens assembly, such as a Fresnel lens, a convex lens, or a concave lens. Alternatively, the light source 230 may be implemented as an assembly with a light guide member to guide the light emitted from the light source 230 in one direction (e.g., toward the photocatalyst filter 240) while preventing the light from leaking in the other directions. At least one parameter among the brightness, temperature, color, light focusing, light emission timing, and light emission direction of the light source 230 may be controlled by the controller 280.

According to an embodiment, the light source 230 may be positioned in front of the photocatalyst filter 240 to emit light to the photocatalyst filter 240. Here, 'front' may be a term used to indicate the position of components on the flow of air flowing in the housing 11 of the electronic device 10. For example, the pre-filter 210, HEPA filter 220, and light source 230 may be disposed in front of the photocatalyst filter 240 and the blower fan 250 may be disposed behind the photocatalyst filter 240. The light source 230 may be disposed in a position spaced apart from the photocatalyst filter 240 by a predetermined distance.

According to various embodiments, the light source 230 may be configured as a light emitting element assembly of a plurality of light emitting elements (e.g., LEDs) disposed in a line (e.g., in the form of a lamp). In FIG. 2, the light source 230 is shown as three lamps, but may be configured of one, two, or four or more lamps. The number and arrangement of the lamps may vary. For example, in FIG. 2, the light source 230 is shown as installed upright in the height direction, but is not necessarily limited thereto, but may be disposed in other various manners (e.g., a lying position). Air purification, deodorization, antibacterial, antifouling, and water purification functions may be performed using the photocatalyst filter 240. For example, the photocatalyst filter 240 may remove harmful substances, such as nitrogen oxides (NOx), sulfur oxides (SOx), formaldehyde, and the like in the air (air purification). Further, the photocatalyst filter 240 may adsorb and/or decompose odors (deodorization), such as acetaldehyde, ammonia, and hydrogen sulfide, and may sterilize various viruses, pathogens and bacteria, prevent decay (antibacterial action), and decompose organic substances, such as cigarette smoke and oil residue (antifouling action) and decompose harmful organic compounds contained in wastewater (water purification).

The photocatalyst filter 240 may include a photocatalyst material for purifying air by reacting with the light emitted from the light source 230. The photocatalyst material includes, but is not limited to, titanium dioxide ($TiO_2$), zinc oxide (ZnO), cadmium sulfide (CdS), tungsten oxide ($WO_3$), or vanadium oxide ($V_2O_3$). Beads (hereinafter, the beads 300 of FIG. 3 described below) may be formed of the photocatalyst material itself or by including the photocatalyst material and other additional materials (e.g., zeolite).

The photocatalyst filter 240 may further include a cover in front and/or behind to prevent leakage of the beads. The cover is a ventilative cover, and may be formed, for example, in the form of a mesh with dense through holes through which air inside the electronic device 10 flows. According to an embodiment, the cover may be integrally formed with the photocatalyst filter 240.

The blower fan 250 may be a component to introduce the air outside the electronic device 10 into the housing 11 through the inlet 12. The air taken in by the blower fan 250 may be purified while passing through various filters (pre-filter 210, HEPA filter 220, and photocatalyst filter 240) and be discharged to the outside of the electronic device 10 through the outlets **13*a* and 13*b*. The blower fan 250 may be operated under the control of the controller 280 and may control the flow of air under the control of the controller 280**.

The first sensor 270 may be a sensor that measures the quality of air inside the electronic device 10. The first sensor 270 may measure the type and concentration of a substance included in the air. The first sensor 270 may be disposed in an inner space of the electronic device 10 (e.g., in a position adjacent to the outlets **13*a* and 13*b* of the electronic device 10). Alternatively, the first sensor 270 may be disposed in a position adjacent to the photocatalyst filter 240 in the inner space of the electronic device 10. The first sensor 270 may be of various types. For example, the first sensor 270 may be a gas sensor driven in various manners including a semiconductor type, a diffusion type, an automatic suction type, an electrochemical type, a catalytic combustion type, or an optical type. The first sensor 270** may be used to detect various gases including hydrogen sulfide (H2S), sulfur dioxide (SO2), hydrogen cyanide (HCN), carbon monoxide (CO), chlorine (Cl2), nitrogen dioxide (NO2), ammonia (NH3), chlorine dioxide (ClO2), ozone (O3), or volatile organic compounds (VOCs).

The controller 280 is a component capable of controlling the overall operation of the electronic device 10. For example, the controller 280 may control driving of the light source 230 and the blower fan 250. According to an embodiment of the disclosure, the controller 280 may determine the quality of air based on the result of detection of the air by the second sensors 22 and 32 of the external electronic devices 20 and 30 and the first sensor 270, and control the light source 230 and/or blower fan 250 of the electronic device 10 according to the quality of air. The controller 280 may also be referred to as a processor. For example, the controller 280 may execute, for example, a program (software) to control at least one other component (e.g., a hardware or software component) of the electronic device 10 coupled with the controller 335, and may perform various data processing or computation. According to an embodiment, as at least part of the data processing or computation, the controller 280 (or processor) may load a command or data received from another component (e.g., the sensor or communication module) onto a volatile memory, process the command or the data stored in the volatile memory, and store resulting data in a non-volatile memory. The controller 280 may include one central processing unit (CPU) (or digital signal processor (DSP), microprocessing unit (MPU), etc.), random access memory (RAM), read-only memory (ROM), and a system bus. The controller 280 may be implemented as a micro computer (MICOM) or an application specific integrated circuit (ASIC).

The controller 280 may implement an air clean mode and a filter recycling mode of the electronic device 10 automatically according to a preset algorithm or according to the user's input, using at least some components described above in connection with FIG. 2. For example, that the electronic device 10 is implemented in the air clean mode may be, for example, to activate both the light source 230 and the blower fan 250 to emit light from the light source 230 to the photocatalyst filter 240 and introduce the external air of the electronic device 10 to the inside of the electronic device 10 through the blower fan 250 to purify the external air. The electronic device 10 implemented in the filter recycling mode may, for example, activate the light source 230 while the blower fan 250 remains in the non-active state to emit light from the light source 230 to the photocatalyst filter 240 to remove the contaminants of the filter. According to an embodiment, the time to activate the light source 230 and emit light to the photocatalyst filter 240 in the filter recycling mode may be set to be longer than the time to activate the light source 230 to emit light to the photocatalyst filter 240 in the air clean mode. Accordingly, in the filter recycling mode, more light may be provided to the photocatalyst filter 240.

According to various embodiments of the disclosure, the air clean mode and the filter recycling mode may include activating other components and performing operations using the same, other than the above-described component activation and operations. For example, as described below with reference to the embodiment of FIGS. 16 to 18, in the filter recycling mode, the blower fan 250 may be activated while the air in the electronic device 10 is allowed to flow in the reverse direction RF and pass through the photocatalyst filter 240, thereby further enhancing the filter recycling efficiency. The filter recycling mode may additionally include a sealing mode to block at least one air passage of the inlet 12 and the outlets 13*a* and 13*b* of the electronic device 10, preventing the contaminants in the air from further flowing into the electronic device 10.

Referring to FIG. 3, the electronic device 10 may perform communication with at least one external electronic device 20 and 30 and transfer information about the electronic device 10 (e.g., information related to the filter replacement time) to at least one external electronic device 20 and 30. Various schemes including wireless communication schemes (e.g., Z-wave, 4LoWPAN, radio frequency identification (RFID), long-term evolution device to device (LTE D2D), Bluetooth low energy (BLE), general package radio service (GPRS), Weightless, ZigBee, Edge Zigbee, ANT+, near-field communication (NFC), infrared data association (IrDA), digital enhanced cordless telecommunication (DECT), wireless local area network (WLAN), Bluetooth, Wi-Fi, Wi-Fi Direct, global system for mobile communication (GSM), universal mobile telecommunications system (UMTS), LTE, WiBRO, Cellular 3rd generation (3G), 4th generation (4G), 5th generation (5G), ultrasound, or such wireless communication), as well as access to the external device through the Internet and short-range communication network (local area network (LAN)) may be applied to communication between the electronic device 10 and the external electronic devices 20 and 30.

FIG. 3 illustrates an air conditioner 20 and a refrigerator 30 as the external electronic devices, but embodiments are not limited thereto. As an external electronic device to perform communication and information transfer with the electronic device 10, any one electronic product of the air conditioner 20 or the refrigerator 30 may be selected. Further, alternatively or additionally, other electronic products may be applied to the external electronic devices 20 and 30 of the disclosure. Examples of the external electronic devices 20 and 30 may vary. For example, the examples may include various electronic products including an air conditioner, a refrigerator, a television (TV) or other various home appliances, a smartphone, a tablet personal computer (PC), a desktop PC, or a laptop computer. The external electronic devices 20 and 30 may include an Internet-of-things (IoT) device. Accordingly, the electronic device 10 may be applied to intelligent services (e.g., smart home, smart city, smart car, or healthcare) based on 5G communication technology and/or IoT-related technology.

According to various embodiments of the disclosure, the external electronic devices 20 and 30 may include display units 21 and 31 and may thereby display the information (e.g., information related to the filter replacement time) received from the electronic device 10.

The external electronic devices 20 and 30 may include second sensors 22 and 32. The second sensors 22 and 32 may be sensors that measure the quality of air outside the electronic device 10. The second sensors 22 and 32 may measure the type and concentration of the substance included in the air outside the electronic device 10. The second sensors 22 and 32 may also be of various types. For example, the second sensors 22 and 32 may be gas sensors driven in various manners including a catalytic combustion type or an optical type.

According to various embodiments of the disclosure, since the second sensors 22 and 32 are disposed outside the electronic device 10 unlike the first sensor 270, the second sensors 22 and 32 may determine the quality of air in positions farther from the filter of the electronic device 10 than the first sensor 270. As the quality of external air of the electronic device 10 is able to be measured using the second sensors 22 and 32, the quality of the air outside the electronic device 10 and the quality of the air flowing in the electronic device 10 may be compared, rendering it possible to determine whether the filter of the electronic device 10 needs to be replaced. A filter recycling and replacing procedure is described below in greater detail with reference to the embodiment of FIG. 8.

Figure 4:
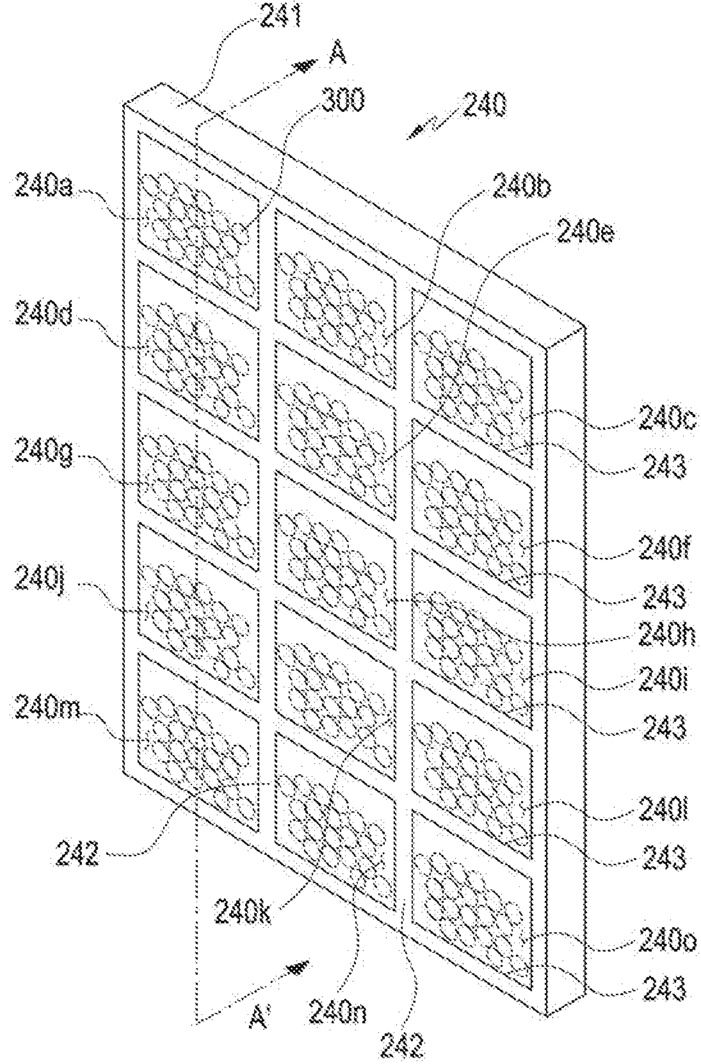
FIG. 4 is a diagram illustrating a photocatalyst filter according to various embodiments of the disclosure.

FIG. 4 is a diagram illustrating a photocatalyst filter 240 according to various embodiments of the disclosure.

The photocatalyst filter 240 may include a body 241 formed with at least one cell 240*a*, 240*b*, 240*c*, 240*d*, 240*e*, 240*f*, 240*g*, 240*h*, 240*i*, 240*j*, 240*k*, 240*l*, 240*m*, 240*n*, and 240*o* through which the air may pass and a plurality of bathers 242 and 243 to define the at least one cell 240*a*, 240*b*, 240*c*, 240*d*, 240*e*, 240*f*, 240*g*, 240*h*, 240*i*, 240*j*, 240*k*, 240*l*, 240*m*, 240*n*, and 240*o* of the body 241. The internal space of the at least one cell 240*a*, 240*b*, 240*c*, 240*d*, 240*e*, 240*f*, 240*g*, 240*h*, 240*i*, 240*j*, 240*k*, 240*l*, 240*m*, 240*n*, and 240*o* may be filled with a plurality of beads 300. The at least one cell 240*a*, 240*b*, 240*c*, 240*d*, 240*e*, 240*f*, 240*g*, 240*h*, 240*i*, 240*j*, 240*k*, 240*l*, 240*m*, 240*n*, and 240*o* is not limited to the embodiment illustrated in the drawings. The at least one cell 240*a*, 240*b*, 240*c*, 240*d*, 240*e*, 240*f*, 240*g*, 240*h*, 240*i*, 240*j*, 240*k*, 240*l*, 240*m*, 240*n*, and 240*o* may be defined in various numbers, shapes, and sizes according to embodiments. The shape and size of the beads 300 received inside the photocatalyst filter 240 may also vary.

The bead 300 is a photocatalyst bead, and may be formed of a photocatalyst material itself or a combination of the photocatalyst material and other additional materials. For example, the bead 300 may include an adsorbent (e.g., zeolite, sepiolite, mesoporous silica ($SiO_2$), silica (SiO2), activated carbon, clay, etc.) as the other additional materials than the photocatalyst material to better adsorb impurities. For example, the bead 300 may be formed by adding a small amount (e.g., about 2 wt % to about 20 wt %) of water and titanium dioxide ($TiO_2$), which is a photocatalyst material, and zeolite. The zeolite may include a natural zeolite or a synthetic zeolite (zeolite A, zeolite X, zeolite Y, ZSM-5 zeolite, or beta zeolite). As another example, the beads 300 may be formed as water and titanium dioxide ($TiO_2$), which is a photocatalyst material, and zeolite are mixed and granulated, sieved and dried. According to various embodiments of the disclosure, the electronic device (e.g., the electronic device 10 of FIG. 1) may be an electronic device of a hybrid type which is a combination of the decomposition type to decompose the contaminants in the air by photocatalyst phenomenon and the adsorption type to adsorb contaminants, as a method (air purification method) to generate clean air by removing the contaminants in the air.

The shape and size of the beads 300 may be appropriately selected depending on the type of gas to be removed, removal rate, or removal rate. The shape of the beads 300 may be, for example, a spherical shape, a cylindrical shape, a hexahedral shape, or a porous shape, and the size of the beads 300 may be, for example, about 0.5 mm to about 5 mm. However, without limited to a specific shape and size, the beads may be formed in any shape and any size. According to various embodiments, the beads 300 may have a smooth surface and may have protrusions on the surface to increase the reaction surface area.

Figure 5:
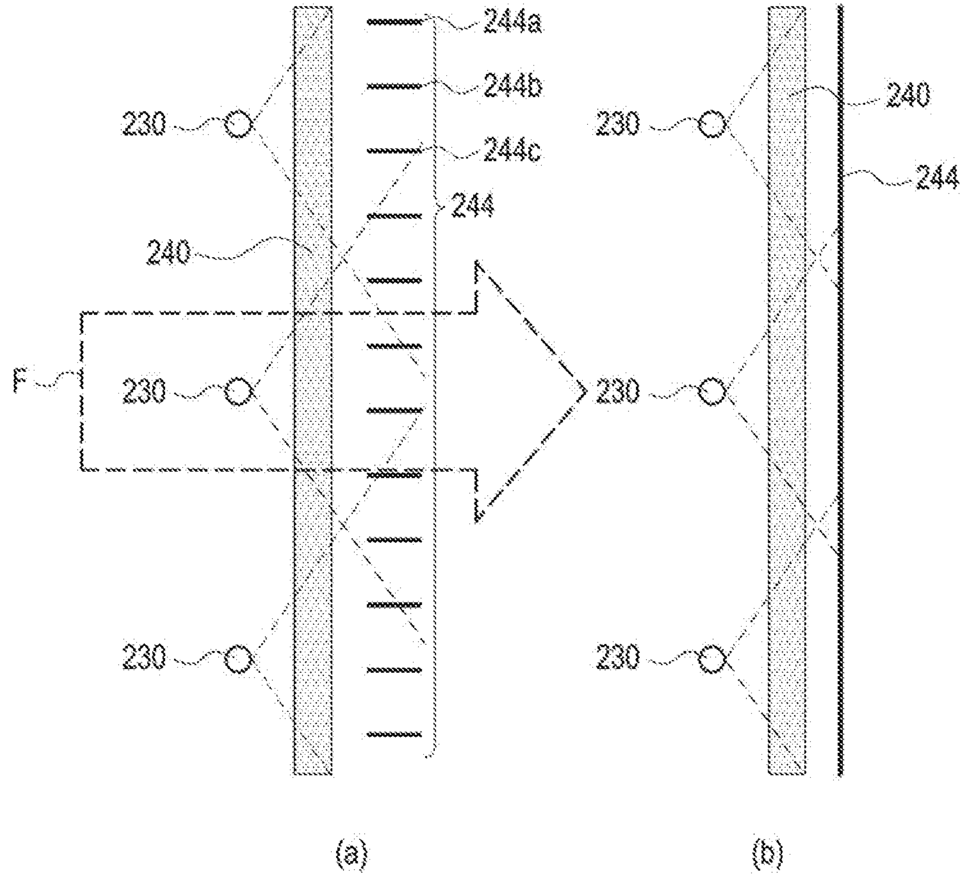
FIG. 5 is a diagram illustrating an example in which a flap assembly is opened or closed according to the flow of the air in the flap assembly in a photocatalyst filter according to various embodiments of the disclosure.

FIG. 5 is a diagram illustrating an example in which an opening/closing part 244 (hereinafter referred to as, "flap assembly 244) is opened or closed according to the flow of the air in the flap assembly 244 in a photocatalyst filter 240 according to various embodiments of the disclosure.

According to an embodiment, the photocatalyst filter 240 may have a flap assembly 244 formed on the rear surface of the body 241. According to an embodiment, the flap assembly 244 may include a plurality of flaps, such as flaps 244*a*, 244*b* and 244*c*, which may be provided in one photocatalyst filter 240. For example, the flap assembly 244 may include the plurality of flaps to be respectively disposed in at least one cell, such as cells 240*a*, 240*b*, 240*c*, 240*d*, 240*e*, 240*f*, 240*g*, 240*h*, 240*i*, 240*j*, 240*k*, 240*l*, 240*m*, 240*n*, and 240*o*, respectively, of the photocatalyst filter 240 to open or close the flow of air flowing in the at least one cell, such as cells 240*a*, 240*b*, 240*c*, 240*d*, 240*e*, 240*f*, 240*g*, 240*h*, 240*i*, 240*j*, 240*k*, 240*l*, 240*m*, 240*n*, and 240*o* (e.g., flap 244*a* may correspond to cell 240*a*, flap 244*b* may correspond to cell 240*b*, flap 244*c* may correspond to cell 240*c*, etc.). According to an embodiment, the flap assembly 244 may be pivotally coupled to one side of the body 241 to be opened as shown in (a) of FIG. 5 or closed as shown in (b) of FIG. 5.

Figure 6:
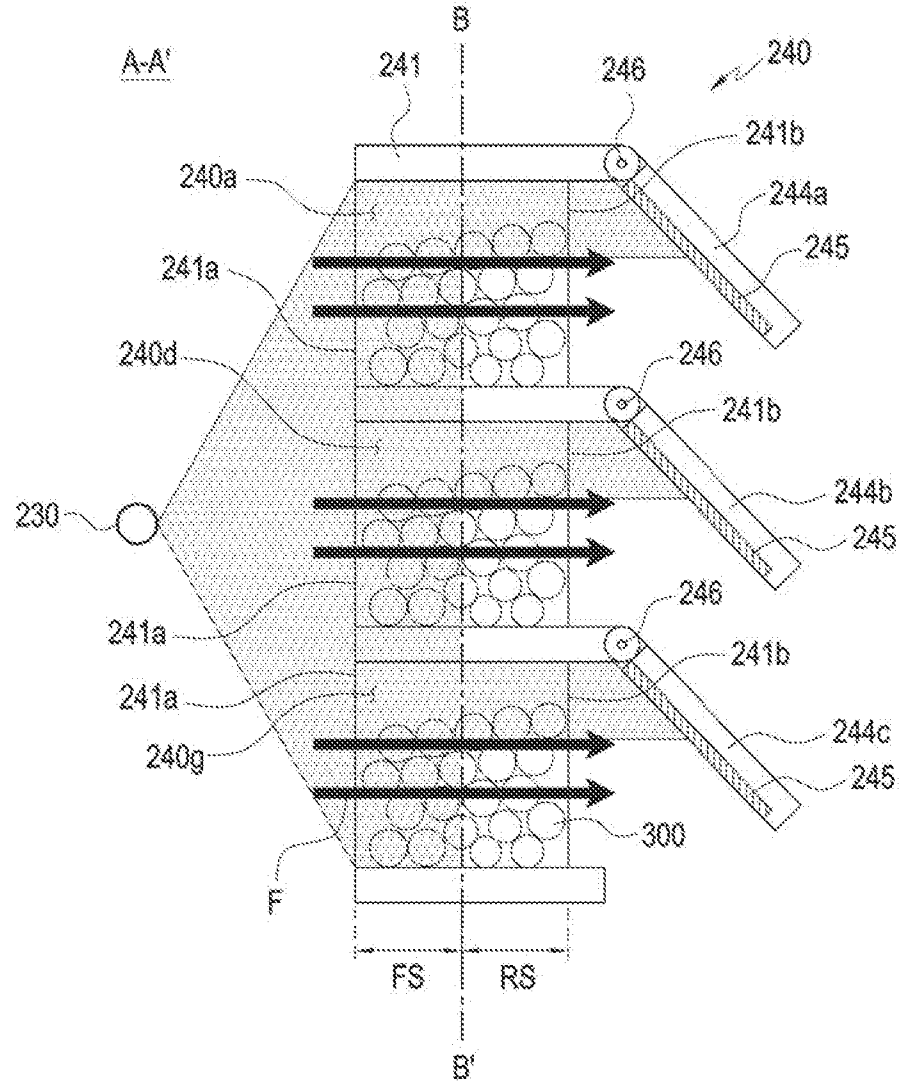
FIG. 6 is a diagram illustrating an opened state of a flap assembly in a photocatalyst filter according to various embodiments of the disclosure.
Figure 7:
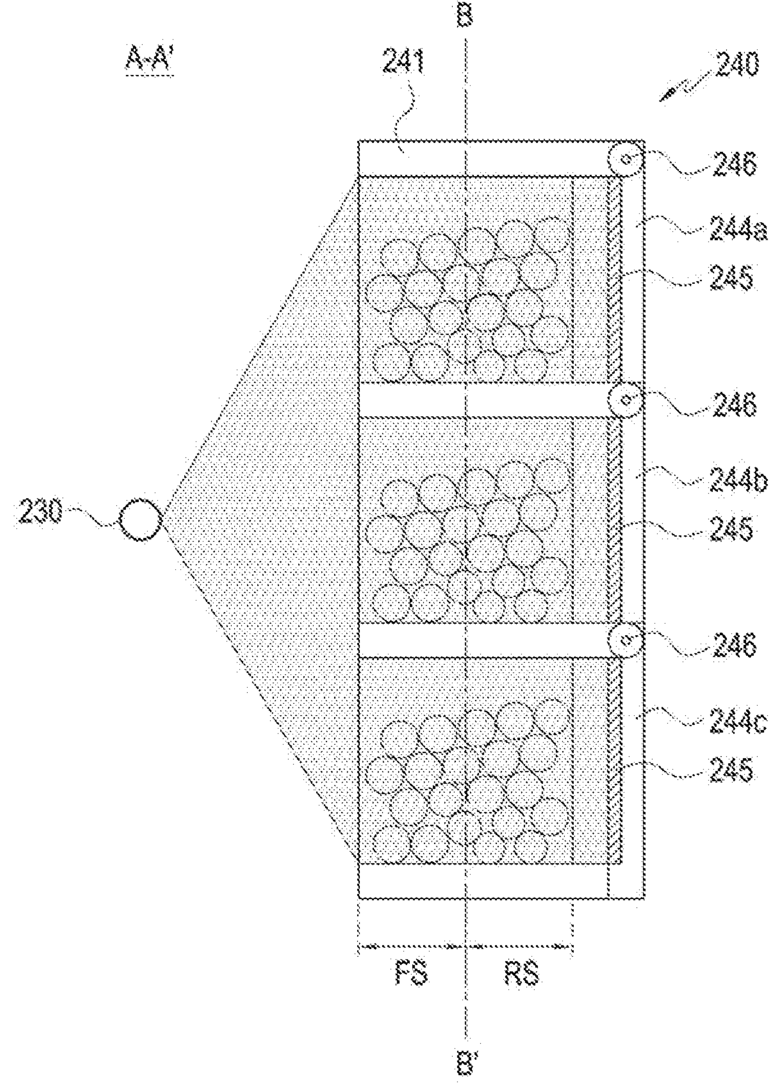
FIG. 7 is a diagram illustrating a closed state of a flap assembly in a photocatalyst filter according to various embodiments of the disclosure.

According to an embodiment, the flap assembly 244 may be disposed in a position spaced apart from the photocatalyst filter 240 by a predetermined distance (e.g., about 0.1 cm to about 3 cm). Although FIGS. 6 and 7 illustrate that the flap assembly 244 is integrally formed with the photocatalyst filter 240, embodiments are not limited thereto. It should be noted that the flap assembly 244 may be provided as a component separated from the photocatalyst filter 240 in the housing.

According to an embodiment, the opening and closing of the flap assembly of FIG. 5 may be performed based on the flow rate of the air passing through the flap assembly 244. For example, when the blower fan 250 intakes a large amount of external air into the inside of the electronic device 10 (i.e., when the electronic device 10 operates in the clean mode), the flap assembly 244 may be opened. In contrast, when the intake of air by the blower fan 250 is not needed (i.e., when the electronic device 10 is powered off (turned off) or operates in the filter recycling mode), the flap assembly 244 may be closed.

According to an embodiment, the opening and closing of the flap assembly 244 may be manually implemented according to the amount of air flowing through the flap assembly 244 inside the electronic device 10. For example, when the blower fan 250 is operated to intake the air into the inside of the electronic device 10, the flap assembly 244 may be forced to be opened by being pushed by the large amount of air flowing from the front to rear of the flap assembly 244. As an example, when the blower fan 250 does not operate or the amount of the air pressurizing the flap assembly 244 is small, the flap assembly 244 is not opened but remains closed. As another example, if the blower fan 250 is operated initially in the closed state of the flap assembly 244 or the amount of air pressurizing the flap assembly 244 increases, the flap assembly 244 may be opened and, when the operation of the blower fan 250 is stopped or the amount of air pressurizing the flap assembly 244 is reduced later, it may be restored from the opened state to the closed state. According to an embodiment, the flap assembly 244 may be formed to be closed by gravity acting on the flap assembly 244 when it is closed.

However, without limitations thereto, according to an embodiment, the opening and closing of the flap assembly 244 may also be implemented by the operation of an active element controlled by the controller 280, such as a motor.

FIG. 6 is a diagram illustrating an opened state of a flap assembly 244 in a photocatalyst filter 240 according to various embodiments of the disclosure. FIG. 7 is a diagram illustrating a closed state of a flap assembly 244 in a photocatalyst filter 240 according to various embodiments of the disclosure. For example, FIGS. 6 and 7 may be schematic cross-sectional views of the photocatalyst filter 240 shown in FIG. 4, taken along A-A'.

According to various embodiments, the body 241 may include a first opening 241*a* formed in the front surface of the body and a second opening 241*b* formed in the rear surface of the body. The air introduced into the electronic device may enter the photocatalyst filter 240 through the first opening 241*a* and be discharged from the photocatalyst filter 240 through the second opening 241*b* in the forward flow.

According to an embodiment, as shown in FIGS. 6 and 7, the flap assembly 244, including flaps 244*a*, 244*b* and 244*c*, may include a hinge structure 246 connected with the body 241 of the photocatalyst filter 240 and, according to another embodiment, the flap assembly 244 may also have a hard plate structure to remain in shape between the opening and the closing. According to an embodiment, the hinge structure 246 may be formed of an elastic material to play a role to open and close the flap assembly 244. However, without limitations thereto, the connection, arrangement, and/or shape of the flap assembly 244 or its surrounding components may vary according to embodiments. The flap assembly 244 may have any component, arrangement, and/or shape as long as it may be opened or closed based on the flow rate of the air passing through the flap assembly 244 and/or the operation of the blower fan 250. For example, the flap assembly 244 may be formed of a thin metal film and be opened or closed according to the flow rate of the air passing through the flap assembly 244 and/or the operation of the blower fan 250. According to an embodiment, when the flap assembly 244 is formed of a thin metal film, the hinge structure 246 may be omitted. For example, the flap assembly 244 may be formed to be opened by the flow rate of the air passing through the first opening 241*a* and the second opening 241*b* and closed by gravity without including a separate hinge structure 246.

The pivot angle of the flap assembly 244 may be formed to be up to 0 degrees to 90 degrees with respect to the closed state of the flap assembly 244, but is not limited thereto. According to various embodiments of the disclosure, the flap assembly 244 may additionally or alternatively include a reflecting plate 245. The reflecting plate 245 may include a plurality of reflecting plates each corresponding to the flaps of the flap assembly 244. For example, each of the flaps 244*a*, 244*b*, and 244*c* may include a respective reflecting plate. According to an embodiment, the reflecting plate 245 may be formed on the front surface of the flap assembly 244 (e.g., the surface in the direction in which the air is introduced toward the flap assembly 244). When the flap assembly 244 is formed for each of at least one cell 240*a*, 240*b*, 240*c*, 240*d*, 240*e*, 240*f*, 240*g*, 240*h*, 240*i*, 240*j*, 240*k*, 240*l*, 240*m*, 240*n*, and 240*o*, the reflecting plate 245 may also be formed on the front surface of the flap assembly 244 of each of the at least one cell 240*a*, 240*b*, 240*c*, 240*d*, 240*e*, 240*f*, 240*g*, 240*h*, 240*i*, 240*j*, 240*k*, 240*l*, 240*m*, 240*n*, and 240*o*.

The reflecting plate 245 may be a component for collecting the light emitted backward from the light source 230 to the photocatalyst filter 240 to the front of each cell of the photocatalyst filter 240. For example, the reflecting plate 245 may collect or not collect the light emitted from the light source 230 toward the beads 300 formed inside the photocatalyst filter 240 according to the opening or closing of the flap assembly 244 (i.e., according to the operation of the blower fan and/or the flow rate of the air passing through the flap assembly 244). For example, as shown in FIG. 6, the reflecting plate 245 may not collect the light emitted from the light source 230 to the beads in the opened state of the flap assembly 244. In contrast, as shown in FIG. 7, the reflecting plate 245 may collect the light emitted from the light source 230 to the beads in the closed state of the flap assembly 244.

The light emitted from the light source 230 may be radially emitted to the photocatalyst filter 240 and be incident on at least one cell 240*a*, 240*b*, and 240*c*. If the light incident on the at least one cell 240*a*, 240*b*, and 240*c* reaches the beads 300 disposed on the space of the at least one cell 240*a*, 240*b*, and 240*c*, the light may react with the photocatalyst material included in the beads 300, creating radicals (e.g., OH) and thereby decomposing the contaminants in the air. Since the at least one cell 240*a*, 240*b*, and 240*c* forms a space with a predetermined depth in the propagation direction of the light, light may not reach the beads 300 positioned at the rear, as compared with the beads 300 positioned at the front in the space in the cell.

For example, as shown in FIG. 6, the at least one cell 240*a*, 240*b*, and 240*c* may be divided into a front section FS and a rear section RS with respect to a virtual line B-B' crossing the middle of the at least one cell 240*a*, 240*b*, and 240*c*. In this case, the light emitted from the light source 230 may reach the beads 300 disposed in the front section FS and rear section RS. According to an embodiment, the light emitted from the light source 230 may partially pass through the front section FS and the rear section RS and reach the back of the photocatalyst filter 240, but not reach the beads 300 disposed at the edge of the rear section RS. In the closed state of the flap assembly 244 with the reflecting plate 245 formed in the flap assembly 244 as shown in FIG. 7, light may be reflected by the reflecting plate 245 to reach the beads 300 disposed at the edge of the rear section RS of the at least one cell 240*a*, 240*b*, and 240*c*.

In other words, when the light source 230 emits light to the photocatalyst filter 240, if the reflecting plate 245 is not formed in the flap assembly 244, or the reflecting plate 245 is formed in the flap assembly 244 but the flap assembly 244 is in the opened state, the range in which the light emitted from the light source 230 reaches the beads 300 inside the photocatalyst filter 240 may be limited to the hatched area as in the embodiment of FIG. 6. In contrast, when the light source 230 emits light to the photocatalyst filter 240 (to the rear), the light is reflected by the reflecting plate 245, so that the range in which the light reaches the beads 300 inside the photocatalyst filter 240 may be extended as in the embodiment of FIG. 7. In the embodiment of FIG. 7, the light emitted from the light source 230 may not only directly reach the beads 300 but also be reflected by the reflecting plate 245 to reach the blind spots inside the photocatalyst filter 240 or the beads 300 positioned in the rear section RS. Resultantly, the number of the beads 300 reacting with the light source 230 increases, enhancing the efficiency of the photocatalyst filter.

As described above, the flap assembly 244 may be disposed in a position spaced apart from the rear surface (or the second opening 241*b*) of the photocatalyst filter 240 by a predetermined distance (e.g., about 0.1 cm to about 3 cm). Accordingly, the reflecting plate 245 may also be formed in a position spaced apart from the rear surface (or the second opening 241*b*) of the photocatalyst filter 240 by a predetermined distance (e.g., about 0.1 cm to about 3 cm). As the reflecting plate 245 is spaced apart from the rear surface (or the second opening 241*b*) of the photocatalyst filter 240 by a predetermined distance, the light reaching the reflecting plate 245 may cover most of the rear area of the photocatalyst filter 240.

According to various embodiments of the disclosure, the reflecting plate 245 may include a reflecting mirror, stainless steel (SUS), aluminum, an aluminum alloy, or such a metal. According to an embodiment, the reflecting plate 245 may be formed of a lightweight polymer sheet or plastic plate. According to an embodiment, the reflecting plate 245 may be formed of a metal foil such as an aluminum foil. The reflecting plate 245 may be integrally formed with the flap assembly 244 and may be a component that substantially replaces the flap assembly 244 playing a role to open/close the air flow. Further, in various embodiments of the disclosure, the flap assembly 244 is formed of a metal foil, such as an aluminum foil, and the reflecting plate 245 corresponds to a metal thin film formed on at least one surface of the foil.

According to various embodiments described above, the photocatalyst filter 240 may be contaminated as the electronic device 10 is used, deteriorating filtering efficiency. For example, the contaminants in the air may be adsorbed to the beads 300 included in the photocatalyst filter 240, and if sufficient light is not received from the light source 230 (e.g., when beads adsorbed with contaminants are present in the blind spots which are not reached by light in the photocatalyst filter), the filtering performance of the photocatalyst filter 240 may not be sufficiently exerted.

When its filtering performance is deteriorated, the filter may be replaced with a new filter directly by the user. In contrast, the disclosure provides various embodiments for a method for automatically recycling the photocatalyst filter with deteriorated filtering performance.

Figure 8:
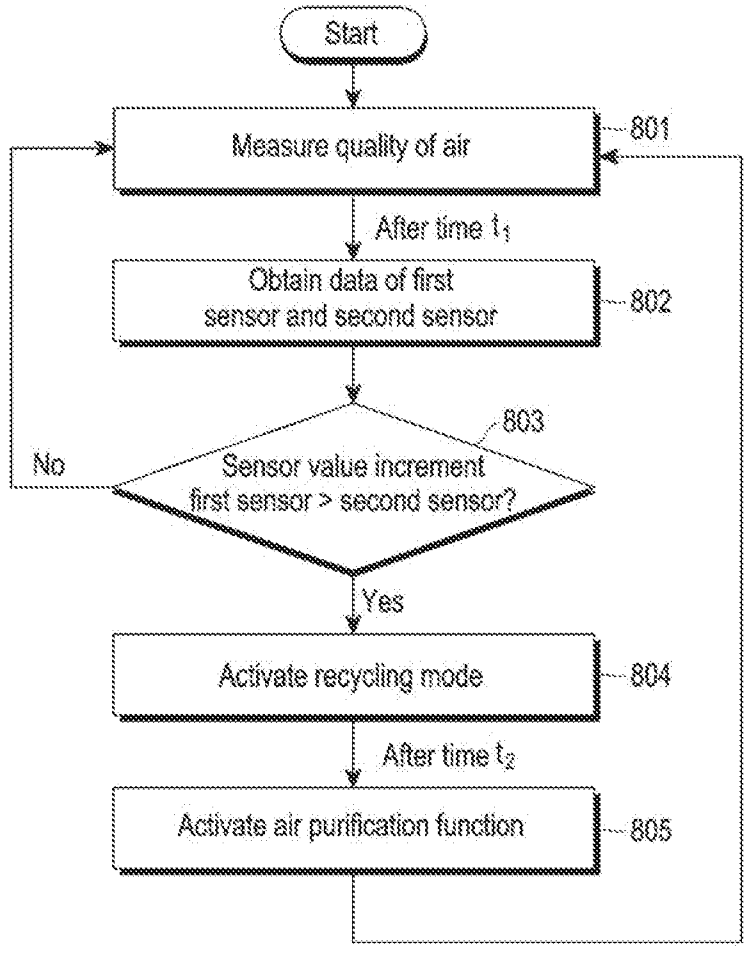
FIG. 8 is a flowchart illustrating a filter recycling procedure according to various embodiments of the disclosure.

FIG. 8 is a flowchart illustrating a filter recycling procedure according to various embodiments of the disclosure;

According to an embodiment of the disclosure, the filter recycling procedure may include at least one of operations 801 to 805.

In operation 801, in the state in which the air clean mode of the electronic device 10 (e.g., air purifier) is terminated (or in a state in which it is not executed), the controller 280 may measure the quality of the internal or ambient air of the electronic device 10 during or for a predetermined time. According to an embodiment, the controller 280 may measure the quality of the internal air of the electronic device 10 and the quality of the external air of the electronic device 10 during or for a predetermined time (e.g., time t1) using the first sensor 270 inside the electronic device 10 and the second sensor 22 and/or 32 of the external electronic device 20 and/or 30.

In operation 802, the first sensor 270 may be used to detect the concentration of a specific contaminant (e.g., gas) in the air inside the electronic device 10, and the second sensor 22 and/or 32 may be used to detect the concentration of a specific contaminant (e.g., gas) in the air outside the electronic device 10 using the second sensor 22 and/or 32. The controller 280 may obtain data related to the contaminant detected by the first sensor 270 and the second sensor 22 and/or 32 and, based thereupon, determine whether the photocatalyst filter 240 is contaminated. The data may include a parameter (e.g., increment in odor or degree of odor) related to the contamination of air inside/outside the electronic device 10. The controller 280 may identify an increment (hereinafter, "sensor value increment") or a decrement (hereinafter, "sensor value decrement") in the parameter over time, using the obtained data.

In operation 803, the sensor value increments the first sensor 270 and the second sensor 22 and/or 32 may be compared. As a result of detection thereof, the degree of contamination of the air inside the electronic device 10 may be measured as larger than the degree of contamination of the air outside the electronic device 10. In other words, the sensor value increment of the first sensor 270 may be measured as larger than the sensor value increment of the second sensor 22 and/or 32. In this case, it may be estimated that contaminants remain on the filter (e.g., photocatalyst filter) disposed inside the electronic device 10 in a state in which the air clean mode of the electronic device 10 is terminated or the air clean mode is not executed. It may be thus estimated that the performance of the filter is deteriorated.

In operation 804, if the performance of the filter is estimated to be deteriorated, the filter recycling mode may be activated. In this case, the filter recycling mode may be automatically executed. Further, notifications for filter recycling may be displayed through the display unit 15 or 115 of the electronic device 10 or the display unit 21 and/or 31 of the external electronic device 20 and/or 30. If the performance of the filter is not estimated to be deteriorated, the system may return to operation 801.

According to various embodiments of the disclosure, when the filter recycling mode is started, filter recycling may be performed by adjusting the amount of light emitted from the light source 230 based on the value of contamination measured through the sensor. As the value of contamination of the filter increases, the light source 230 may emit more light (or stronger light). In the filter recycling mode, the operation of the blower fan 250 may be stopped. As described above in connection with various embodiments described above, in the filter recycling mode, the flap assembly 244 may be closed, and the light emitted from the light source 230 may be reflected by the reflecting plate 245 to evenly reach the beads 300, leading to increased filtering efficiency of the photocatalyst filter 240.

In operation 805, after entering the filter recycling mode for a predetermined time (e.g., time t2), or after filter recycling is terminated by the user's input, the electronic device 10 may activate the air purification function using the recycled filter.

Figure 9:
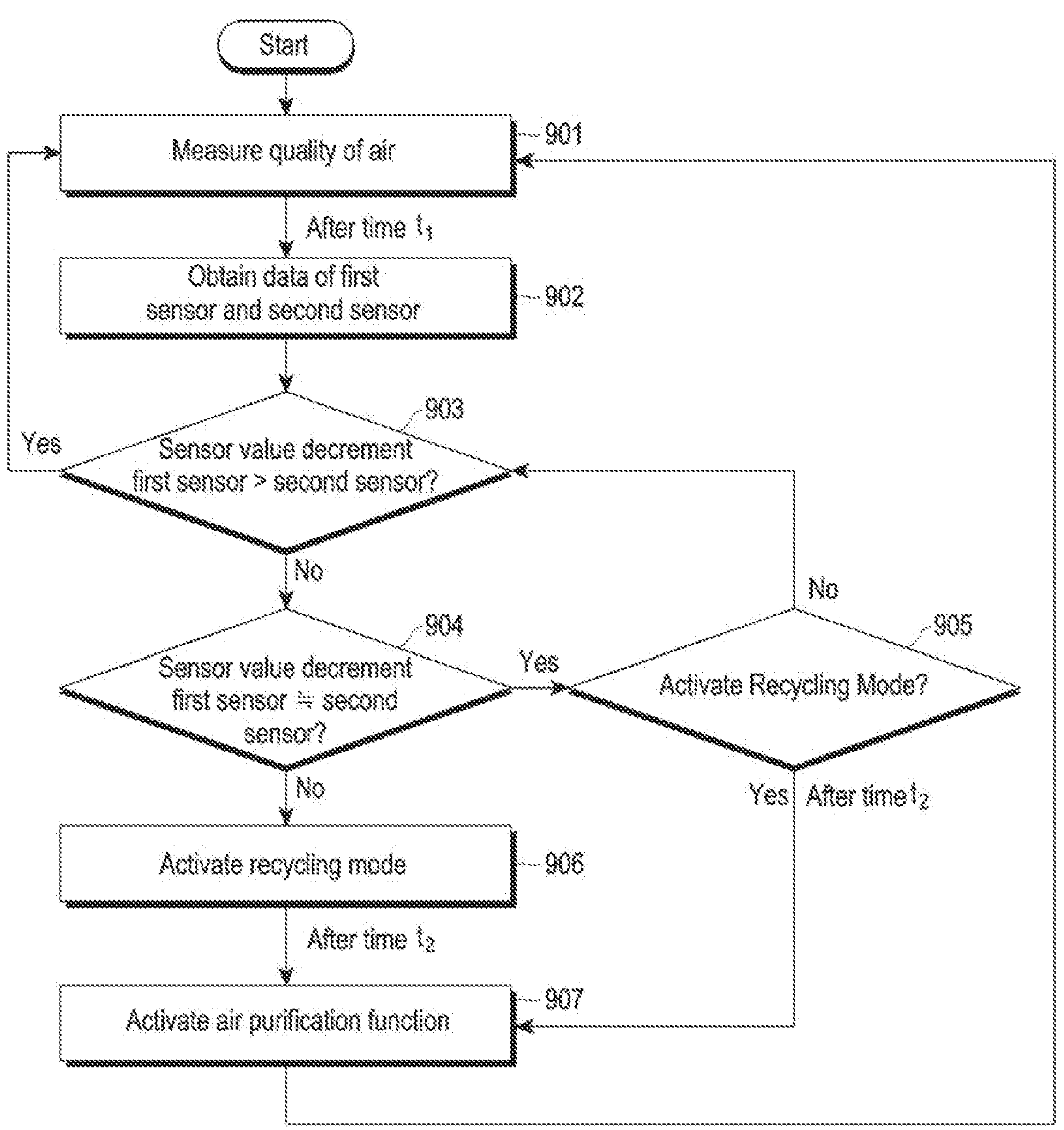
FIG. 9 is a flowchart illustrating a filter recycling procedure according to various embodiments of the disclosure.

FIG. 9 is a flowchart illustrating a filter recycling procedure according to various embodiments of the disclosure.

According to another embodiment of the disclosure, the filter recycling procedure may include at least one of operations 901 to 907.

In operation 901, in the state in which the air clean mode of the electronic device 10 (e.g., air purifier) is running, the controller 280 may measure the quality of the internal or ambient air of the electronic device 10 during or for a predetermined time. According to an embodiment, the controller 280 may measure the quality of the internal air of the electronic device 10 and the quality of the external air of the electronic device 10 during or for a predetermined time (e.g., time t1) using the first sensor 270 inside the electronic device 10 and the second sensor 22 and/or 32 of the external electronic device 20 and/or 30.

In operation 902, the first sensor 270 may be used to detect the concentration of a specific contaminant (e.g., gas) in the air inside the electronic device 10, and the second sensor 22 and/or 32 may be used to detect the concentration of a specific contaminant (e.g., gas) in the air outside the electronic device 10 using the second sensor 22 and/or 32. The controller 280 may obtain data related to the contaminant detected by the first sensor 270 and the second sensor 22 and/or 32 and, based thereupon, determine whether the photocatalyst filter 240 is contaminated. The data may include a parameter (e.g., increment in odor or degree of odor) related to the contamination of air inside/outside the electronic device 10. The controller 280 may identify an increment or a decrement in the parameter over time, using the obtained data. Operation 902 may be the same as operation 802 of the above-described embodiment.

In operation 903, the sensor value decrements of the first sensor 270 and the second sensor 22 and/or 32 may be compared. A decrease in the sensor value may indicate a decrease in contaminants detected by the sensor. In other words, a large decrease in the sensor value may indicate that the contaminant removal function is smoothly performed. For example, when the sensor value decrement of the first sensor 270 is larger than the sensor value decrement of the second sensor 22 and/or 32, it may indicate that the contaminant removal performance of the photocatalyst filter 240 around the first sensor 270 is good. If the sensor value decrement of the first sensor is greater than the sensor value decrement of the second sensor, the system may return to operation 901.

In contrast, in operation 904, it may be determined whether the sensor value decrement of the first sensor 270 is similar to the sensor value decrement of the second sensor 22 and/or 32.

In operation 904, the system may determine whether the sensor value decrement of the first sensor 270 is similar to the sensor value decrement of the second sensor 22 and/or 32. In operation 905, when the sensor value decrement of the first sensor 270 is similar to the sensor value decrement of the second sensor 22 and/or 32, it may be determined whether to activate the recycling mode. That is, it may be estimated that the performance of the photocatalyst filter is deteriorated such that the filtering function is not normally operated. The sensor value decrements of the two sensors may be determined to be similar when the sensor value decrements have a difference by a preset error range. In this case, in operation 905, if the performance of the filter is estimated to be deteriorated, the filter recycling mode may be activated. Further, a notification for filter recycling may be displayed to allow the user to recognize the necessity of filter recycling or to recognize that the air clean function may not be normally operated. In operation 905, it may be determined whether to activate the filter recycling mode according to the user's selection. The filter recycling mode may be activated for a predetermined time (e.g., time t2) and then operation 907 may be performed. When it is determined that the recycling is not required, the system may return to operation 901.

In operation 906, when the sensor value decrement of the first sensor 270 is smaller than the sensor value decrement of the second sensor 22 and/or 32, the recycling mode may be activated. That is, it may be estimated that the filtering function of the photocatalyst filter is not normally operated. In this case, it may be estimated that the performance of the filter is further deteriorated than when determined at operation 904. Thus, the filter recycling mode may be activated, and may be activated automatically.

In operation 907, after entering the filter recycling mode for a predetermined time (e.g., time t2), or after filter recycling is terminated by the user's input, the electronic device 10 may activate the air purification function using the recycled filter.

Figure 10:
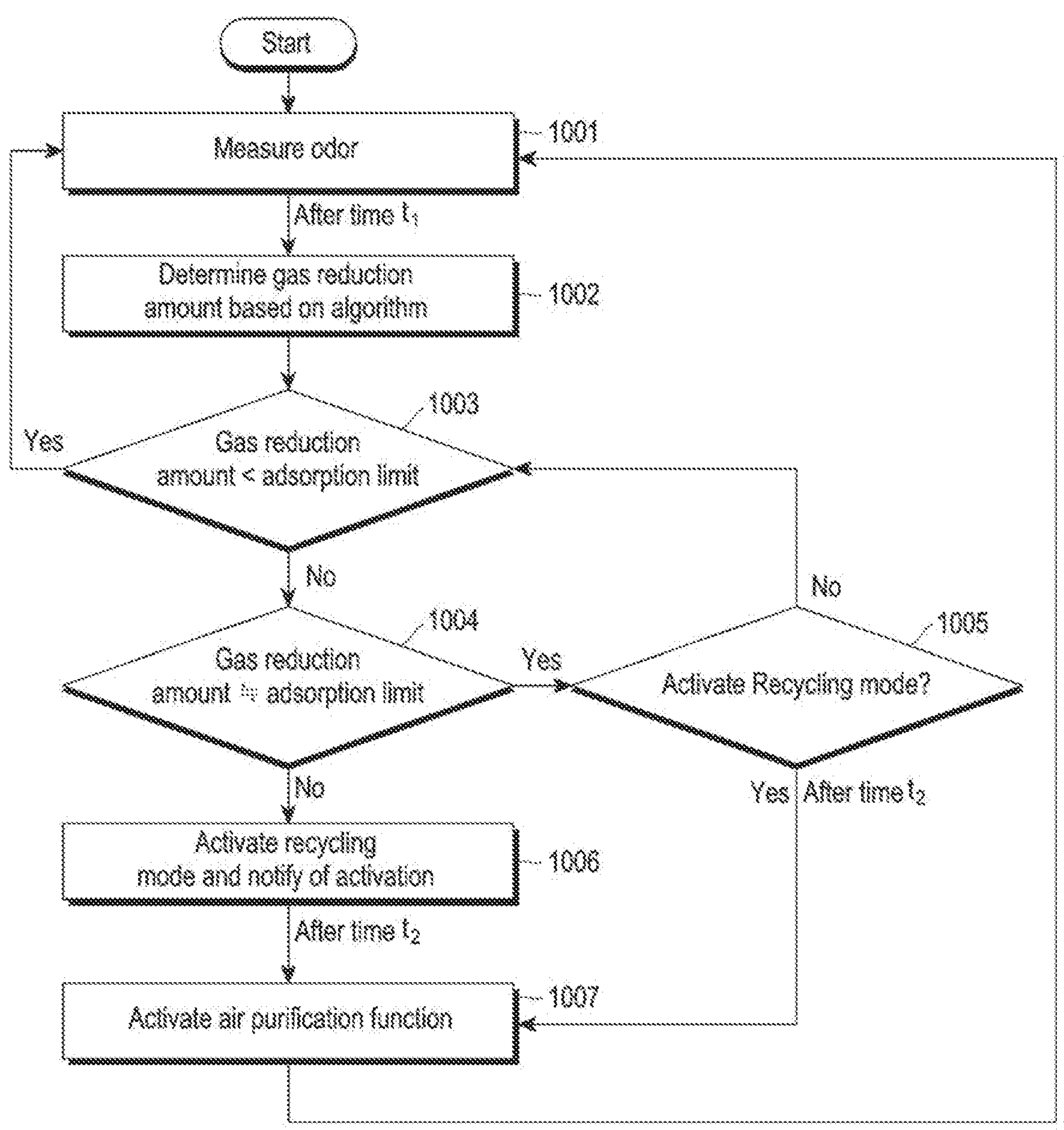
FIG. 10 is a flowchart illustrating a filter recycling procedure according to various embodiments of the disclosure.

FIG. 10 is a flowchart illustrating a filter recycling procedure according to various embodiments of the disclosure.

According to another embodiment of the disclosure, the filter recycling procedure may include at least one of operations 1001 to 1007.

In operation 1001, in the state in which the air clean mode of the electronic device 10 (e.g., air purifier) is running, the controller 280 may measure the quality of the internal or ambient air of the electronic device 10 during or for a predetermined time. In an embodiment, the electronic device 10 may not necessarily require the state in which the air clean mode is operated. For example, operation 1001 may be implemented in a state where the air clean mode of the electronic device is terminated or a state in which the air clean mode is not executed. The controller 280 may measure the quality of the internal air of the electronic device 10 and the quality of the external air of the electronic device 10 during or for a predetermined time (e.g., time t1) using the first sensor 270 inside the electronic device 10 and the second sensor 22 and/or 32 of the external electronic device 20 and/or 30.

In operation 1002, the controller 280 may determine the amount of gas to be reduced (hereinafter, referred to as "gas reduction amount") when the air clean mode of the electronic device 10 is operated, based on a preset algorithm of the sensor and using the data obtained from the first sensor 270. The preset algorithm of the sensor may be an algorithm related to the amount to be reduced per type of gas within a predetermined time. The algorithm may be stored in the controller 280 or a memory of a sensor integrated circuit (IC) provided separately in the sensor. According to the algorithm, it may be determined which gas has been reduced and by which amount while the air clean function is running.

In operation 1003, the controller 280 may compare the gas reduction amount of a specific gas (e.g., 60 ppm for toluene) with the adsorption limit of the photocatalyst filter 240. For example, the adsorption limit for a specific gas may be preset when the photocatalyst filter 240 is manufactured. For example, when the gas reduction amount is smaller than the adsorption limit, it may be determined that the filtering performance of the photocatalyst filter 240 is effective. If the gas reduction amount is less than the absorption limit, the system may return to operation 1001.

In operations 1004, if the gas reduction amount is not less than the absorption limit, the system may determine whether the gas reduction amount is similar to the adsorption limit. When the gas reduction amount is similar to the adsorption limit, in operation 1005, it may be determined whether to activate the recycling mode. That is, it may be predicted to approach the filtering limit of the photocatalyst filter. That the gas reduction amount is similar to the adsorption limit may indicate that there is a difference by a preset error range. In this case, in operation 1005, if the performance of the filter is estimated to be deteriorated, the filter recycling mode may be activated. Further, a notification for filter recycling may be displayed to allow the user to recognize the necessity of filter recycling or to recognize that the air clean function may not be normally operated. In operation 1005, it may be determined whether to activate the filter recycling mode according to the user's selection. If the recycling mode is not activated, then the system may return to operation 1003. If the recycling mode is activate, the system may perform recycling for a predetermined time period (e.g., time t2).

In operation 1006, when the gas reduction amount is larger than the adsorption limit, the recycling mode may be activated and a notification of the activation may be provided. That is, it may be predicted that the photocatalyst filter exceeds the filtering limit such that the performance of the filter is to be deteriorated. In this case, the filter recycling mode may be automatically activated.

In operation 1007, after entering the filter recycling mode for a predetermined time (e.g., time t2), or after filter recycling is terminated by the user's input, the electronic device 10 may activate the air purification function using the recycled filter.

Figure 11:
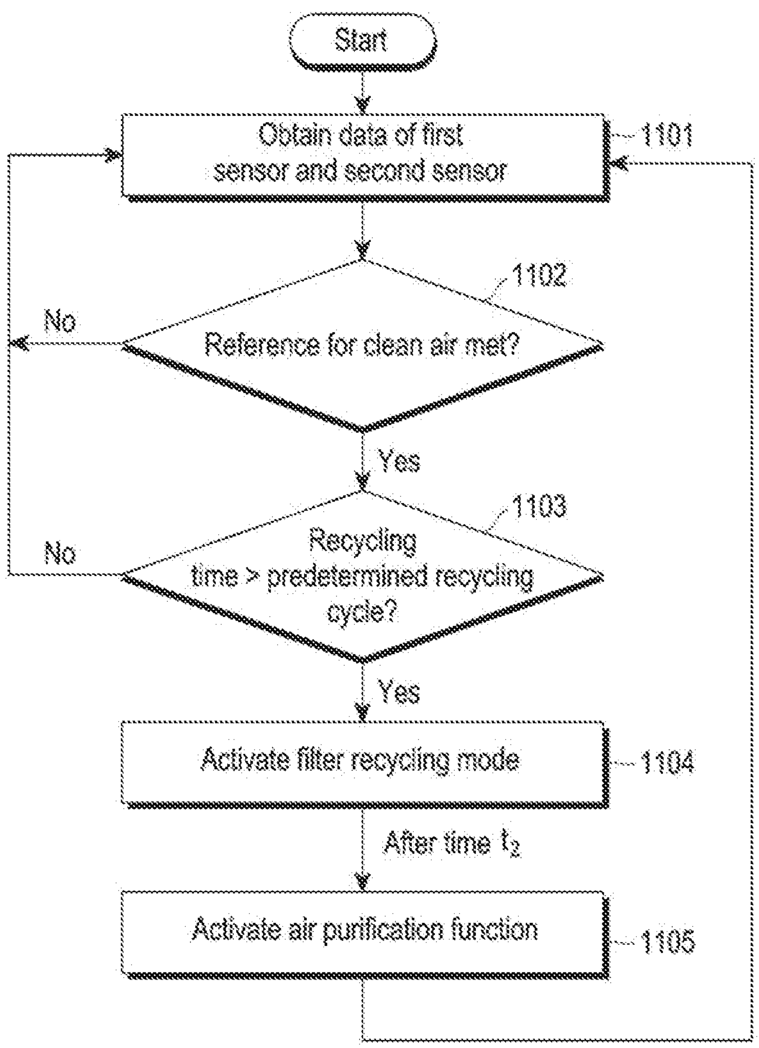
FIG. 11 is a flowchart illustrating a filter recycling procedure according to various embodiments of the disclosure.

FIG. 11 is a flowchart illustrating a filter recycling procedure according to various embodiments of the disclosure.

In operation 1101, the controller 280 may measure the quality of air inside and around the electronic device 10 during or for a predetermined time. Data for the quality of the internal air of the electronic device 10 using the first sensor 270 and the quality of the external air of the electronic device 10 using the second sensor 22 and/or 32 may be obtained.

In operation 1102, the controller 280 may determine whether the ambient air of the electronic device 10 meets a reference for clean air based on the data obtained in relation to the air quality in the first sensor 270 and the second sensor 22 and/or 32. Determining whether the reference for clean air is met may be performed for forming an optimal environment to recycle the filter. When the reference for clean air is not met, the system may return to operation 1101.

When the ambient air of the electronic device 10 is determined to be clean (i.e., when the reference for clean air is met in operation 1102), it may be additionally determined whether the recycling (or replacement) of the photocatalyst filter exceeds a predetermined time in operation 1103. For example, when the photocatalyst filter does not exceed a predetermined recycling cycle or replacement cycle, the filtering performance of the photocatalyst filter may be estimated to be effective and, when exceeding the predetermined recycling cycle or replacement cycle of the filter, the filtering performance of the photocatalyst filter may be estimated to be deteriorated. When the recycling time does not exceed the predetermined recycling cycle, the system may return to operation 1101.

In operation 1104, when the photocatalyst filter exceeds the predetermined recycling cycle or replacement cycle, the filter recycling mode may be activated. Further, a notification for filter recycling may be displayed to allow the user to recognize the necessity of filter recycling or to recognize that the air clean function may not be normally operated.

In operation 1105, after entering the filter recycling mode for a predetermined time (e.g., time t2), or after filter recycling is terminated by the user's input, the electronic device 10 may activate the air purification function using the recycled filter.

Hereinafter, various examples for increasing the filtering efficiency of the photocatalyst filter may be described. For example, the embodiments of FIGS. 12 to 15 may provide various examples of increasing photocatalyst filter efficiency by way of the light source 230. The embodiments of FIGS. 16 to 18 may provide various examples of increasing photocatalyst filter efficiency by changing the blowing direction of the blower fan 250. The embodiment of FIG. 19 may provide various examples of increasing photocatalyst filter efficiency by applying a photocatalyst filter according to an embodiment different from the previous embodiments.

Figure 12:
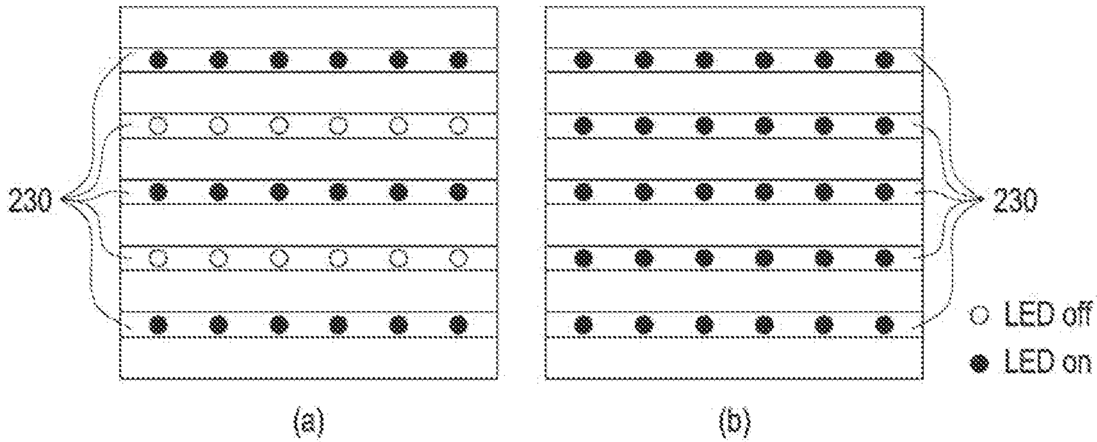
FIG. 12 is a diagram illustrating a method for increasing the photocatalyst filter recycling efficiency using a light source according to various embodiments of the disclosure.
Figure 13:
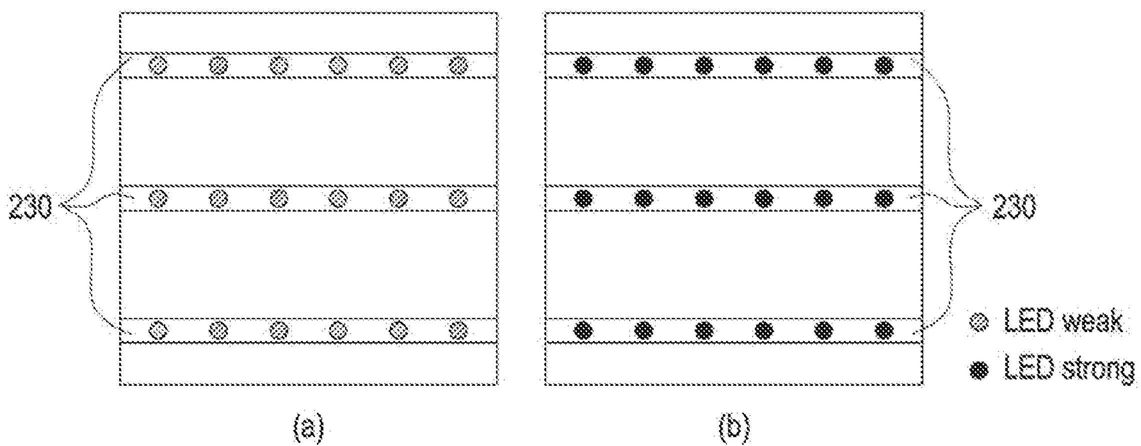
FIG. 13 is a diagram illustrating a method for increasing the photocatalyst filter recycling efficiency using a light source according to various embodiments of the disclosure.
Figure 14:
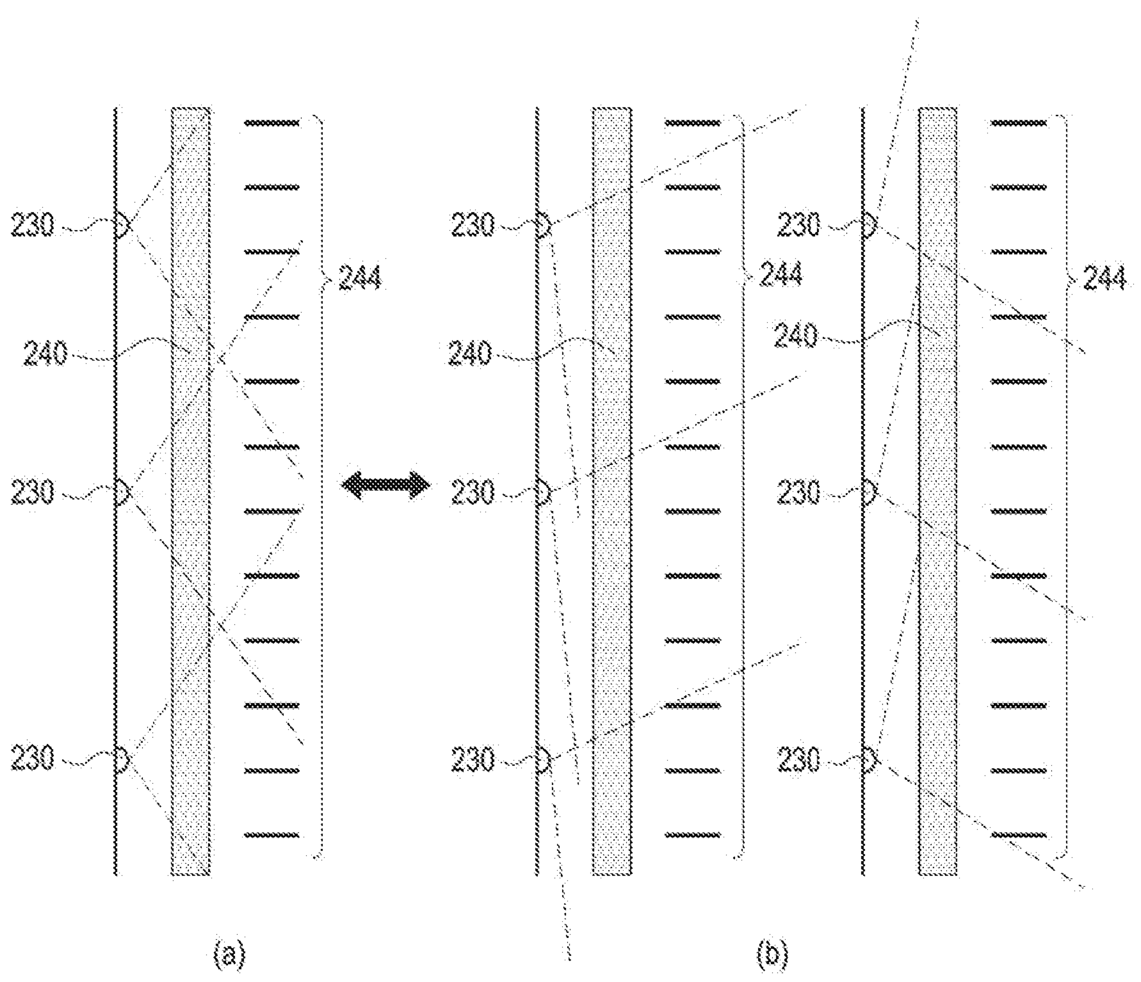
FIG. 14 is a diagram illustrating a method for increasing the photocatalyst filter recycling efficiency using a light source according to various embodiments of the disclosure.
Figure 15:
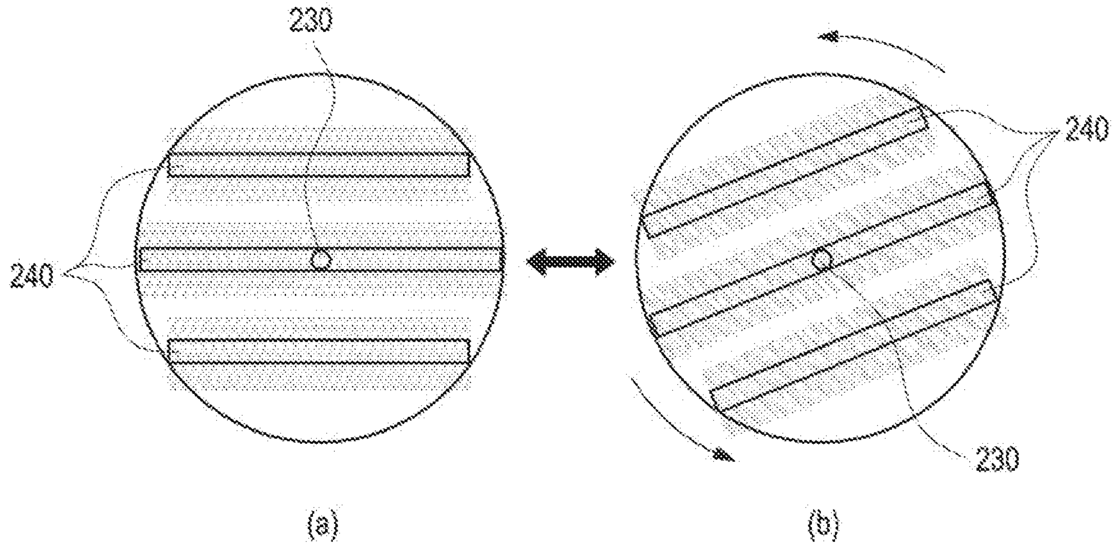
FIG. 15 is a diagram illustrating a method for increasing the photocatalyst filter recycling efficiency using a light source according to various embodiments of the disclosure.

FIG. 12 is a diagram illustrating a method for increasing the photocatalyst filter recycling efficiency using a light source according to various embodiments of the disclosure. FIG. 13 is a diagram illustrating a method for increasing the photocatalyst filter recycling efficiency using a light source according to various embodiments of the disclosure. FIG. 14 is a diagram illustrating a method for increasing the photocatalyst filter recycling efficiency using a light source according to various embodiments of the disclosure. FIG. 15 is a diagram illustrating a method for increasing the photocatalyst filter recycling efficiency using a light source according to various embodiments of the disclosure.

FIGS. 12 to 15 illustrate various embodiments to increase the amount of light that is incident on the photocatalyst filter 240 and reaches the beads 300 using, for example, the number of light emitting elements of the light source 230 positioned in front of the photocatalyst filter 240, intensity of light emissions, or variations in incidence angle.

Referring to FIG. 12, when a plurality of light sources 230 are present in the electronic device 10, and the plurality of light sources 230 each include a plurality of light emitting elements (e.g., LEDs), the amount of light may be increased by increasing the number of light emitting elements that emit light.

Referring to FIG. 13, when the intensity of the light emitted from the light source 230 is adjustable, it is possible to increase the photocatalyst filter efficiency by emitting stronger light from the light source 230.

The embodiment of FIGS. 12 and 13 illustrate operations in the filter recycling mode of the photocatalyst filter 240. According to the embodiment of FIGS. 12 and 13, it is possible to more quickly recycle the photocatalyst filter 240 by increasing more light radiations to the photocatalyst filter 240 than the light radiations from the light source 230 in the air clean mode.

According to various embodiments, the above-described embodiment of FIG. 10 may be described with reference to the embodiment of FIG. 13. It is possible to emit weak light from the light source 230 as shown in (a) of FIG. 13 when the recycling of the filter 240 is performed in a state in which the amount of gas adsorbed to the photocatalyst filter 240 is small and emit strong light from the light source 230 as shown in (b) of FIG. 13 when the recycling of the filter 240 is performed in a state in which the amount of gas adsorbed to the photocatalyst filter 240 is large.

Referring to FIGS. 14 and 15, it is possible to increase the efficiency of the photocatalyst filter by increasing the amount of light reaching the internal space of the photocatalyst filter by changing the light emission direction of the light source 230. That is, in FIG. 14, the light emission direction of the light source 230 may be changed. In FIG. 15, as shown in (a), the light source 230 may be positioned in the middle of filters 240, and, as shown in (b), the angle of the filters 240 may be rotated, causing the light emission direction of the light source 230 to be changed. A method for changing the radiation direction of the light source 230 may be varied according to embodiments as shown in FIGS. 14 and 15.

Figure 16:
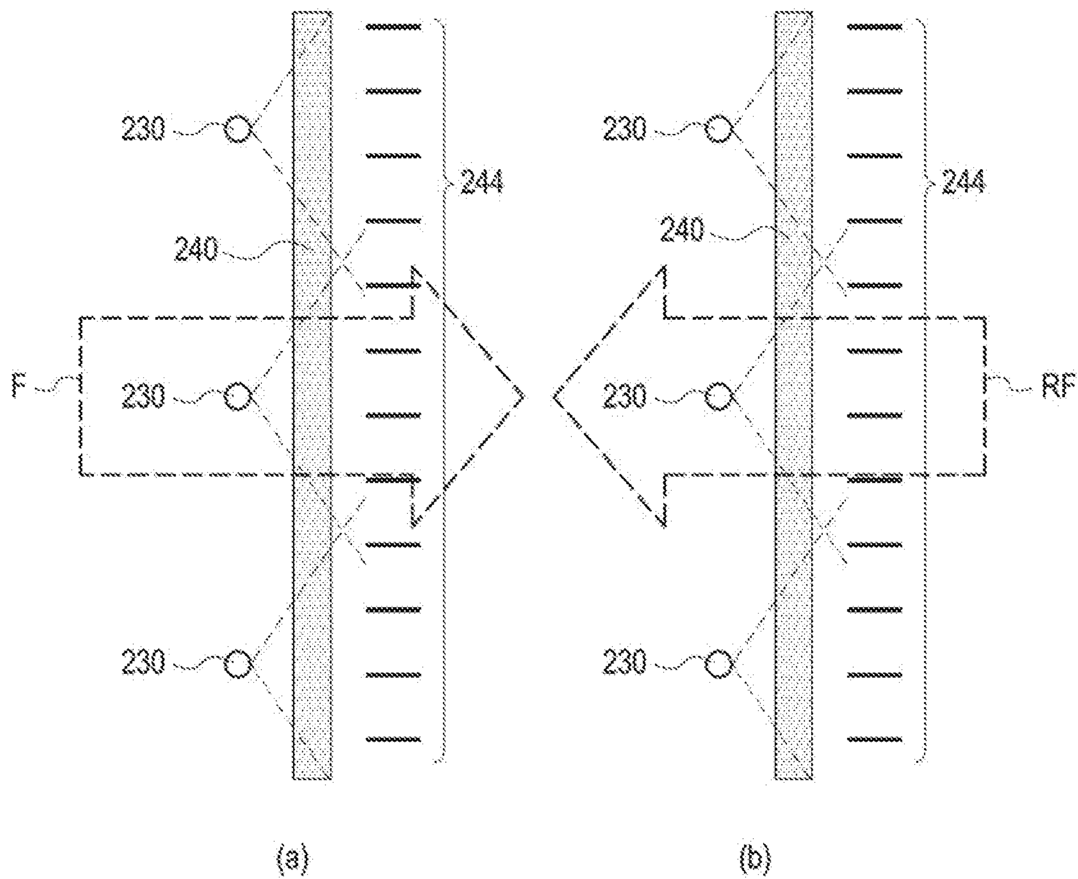
FIG. 16 is a diagram illustrating an example in which the air flows in a forward direction F or reverse direction RF through at least one cell of a photocatalyst filter according to various embodiments of the disclosure.
Figure 17:
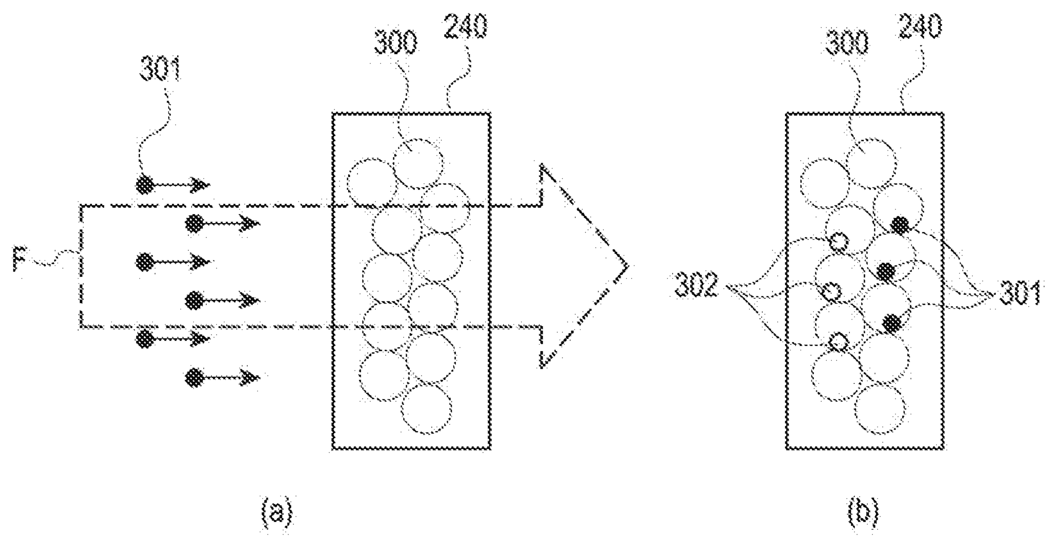
FIG. 17 is a diagram illustrating an example in which particles in the air are adsorbed to beads when the air flows in a forward direction F according to various embodiments of the disclosure.
Figure 18:
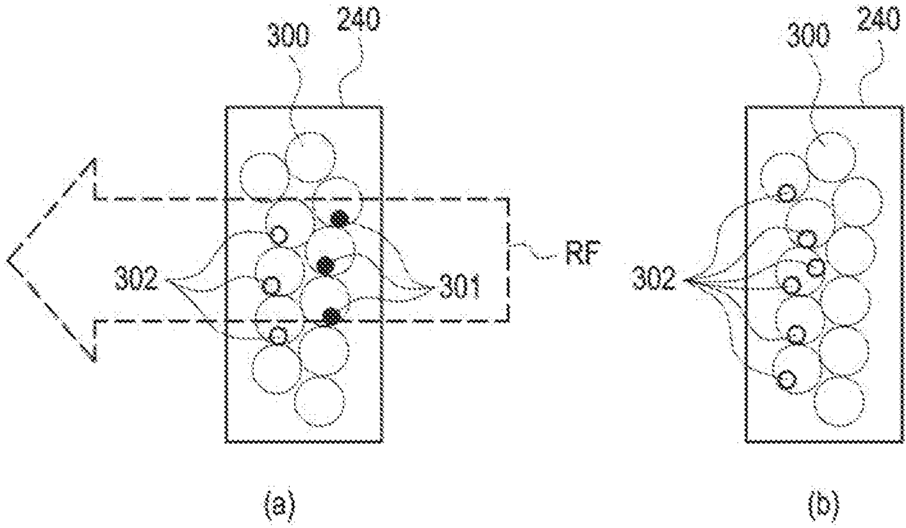
FIG. 18 is a diagram illustrating an example in which particles in the air are adsorbed to beads when the air flows in a reverse direction RF according to various embodiments of the disclosure.

FIG. 16 is a diagram illustrating an example in which the air flows in a forward direction F or reverse direction RF through at least one cell of a photocatalyst filter according to various embodiments of the disclosure. FIG. 17 is a diagram illustrating an example in which particles in the air are adsorbed to beads when the air flows in a forward direction F according to various embodiments of the disclosure. FIG. 18 is a diagram illustrating an example in which particles in the air are adsorbed to beads when the air flows in a reverse direction RF according to various embodiments of the disclosure.

The air flowing in the electronic device 10 may pass through at least one cell of the photocatalyst filter 240 and flow in the forward direction F by the operation of the blower fan 250 or flow in the reverse direction RF which is opposite to the forward direction F by the operation of the blower fan 250.

For example, the blower fan 250 may introduce the air from outside of the electronic device, and the air introduced into the internal space of the electronic device 10 may flow in the forward direction F from the inlet to the outlet. The electronic device 10 may purify the external air of the electronic device 10 through the air flow in the forward direction F (e.g., when the air clean mode is activated). Referring back to FIG. 6 in the forward direction F flow, the air may sequentially pass through the first opening 241*a* and the second opening 241*b* of the photocatalyst filter 240.

As another example, the blower fan 250 may flow the air in the reverse direction RF as opposed to the flow in the forward direction. According to an embodiment, it is possible to flow the air present in the electronic device 10 in the reverse direction RF during or for a predetermined time, by use of the blower fan 250. According to another embodiment, it is also possible to introduce the air from outside of the electronic device through the reverse direction RF flow using the blower fan 250. In this case, the air introduced into the internal space of the electronic device 10 may flow in the reverse direction from the outlet to the inlet. The electronic device 10 may remove the contaminants adsorbed in the filter through the air flow in the reverse direction RF (e.g., in the filter recycling mode). Referring back to FIG. 6, in the reverse direction RF flow, the air may sequentially pass through the second opening 241*b* and the first opening 241*a* of the photocatalyst filter 240.

In the filter recycling mode, as in the embodiment shown in (b) of FIG. 16, and FIGS. 17 and 18, the electronic device 10 may allow the air to flow in the reverse direction RF, leading to desorption of the contaminants adsorbed in the rear section of the photocatalyst filter 240. It is possible to implement a process for delivering the contaminants, which are adsorbed to the beads in the rear section of the photocatalyst filter 240 and are thus not decomposed due to the reverse flow RF of the air, to the beads in the front section and decomposing them.

Referring to (a) of FIG. 17, the air introduced into the inside of the electronic device 10 in the forward F air flow may contain a plurality of contaminant particles 301. The plurality of contaminant particles 301 may be evenly adsorbed over the entire area of the plurality of beads 300 disposed in the photocatalyst filter 240 as shown in (b) of FIG. 17. For example, as described above in connection with the embodiment of FIGS. 6 and 7, in the recycling process of the photocatalyst filter 240, some of the plurality of contaminant particles 301 may be contaminant-free particles 302, but others (e.g., the particles 301 positioned in the rear section of the photocatalyst filter 240) far from the section where the light source 230 is disposed, may remain contaminated despite the filter recycling process.

According to various embodiments of the disclosure, it is possible to remove the contaminants adsorbed to the photocatalyst filter 240 by reversing the blowing direction of the blower fan 250 in the recycling mode of the photocatalyst filter 240. The embodiment of (a) of FIG. 18 and (b) of FIG. 18 may be performed continuously and subsequently to the recycling process of the photocatalyst filter 240 according to the embodiment of (a) of FIG. 17 and (b) of FIG. 17 described above.

Referring to (a) of FIG. 18, the contaminants 301 adsorbed to the beads 300 in the rear section in the photocatalyst filter 240 may be moved to the front section in the photocatalyst filter 240 in the process of the reverse F air flow. Referring to (a) of FIG. 18 and (b) of FIG. 18, the particles 301 positioned in the rear section of the photocatalyst filter 240 may be moved to the front section of the photocatalyst filter 240, and the contaminants may be removed by the photocatalyst reaction. Thus, it is possible to effectively remove the contaminants adsorbed to the beads 300.

According to an embodiment, the filter recycling mode using the reverse flow according to the embodiment of FIGS. 16 to 18 may be operated only when the degree of contamination in the indoor air is lower than a predetermined value through at least one sensor 270, 22, and 32.

Figure 19:
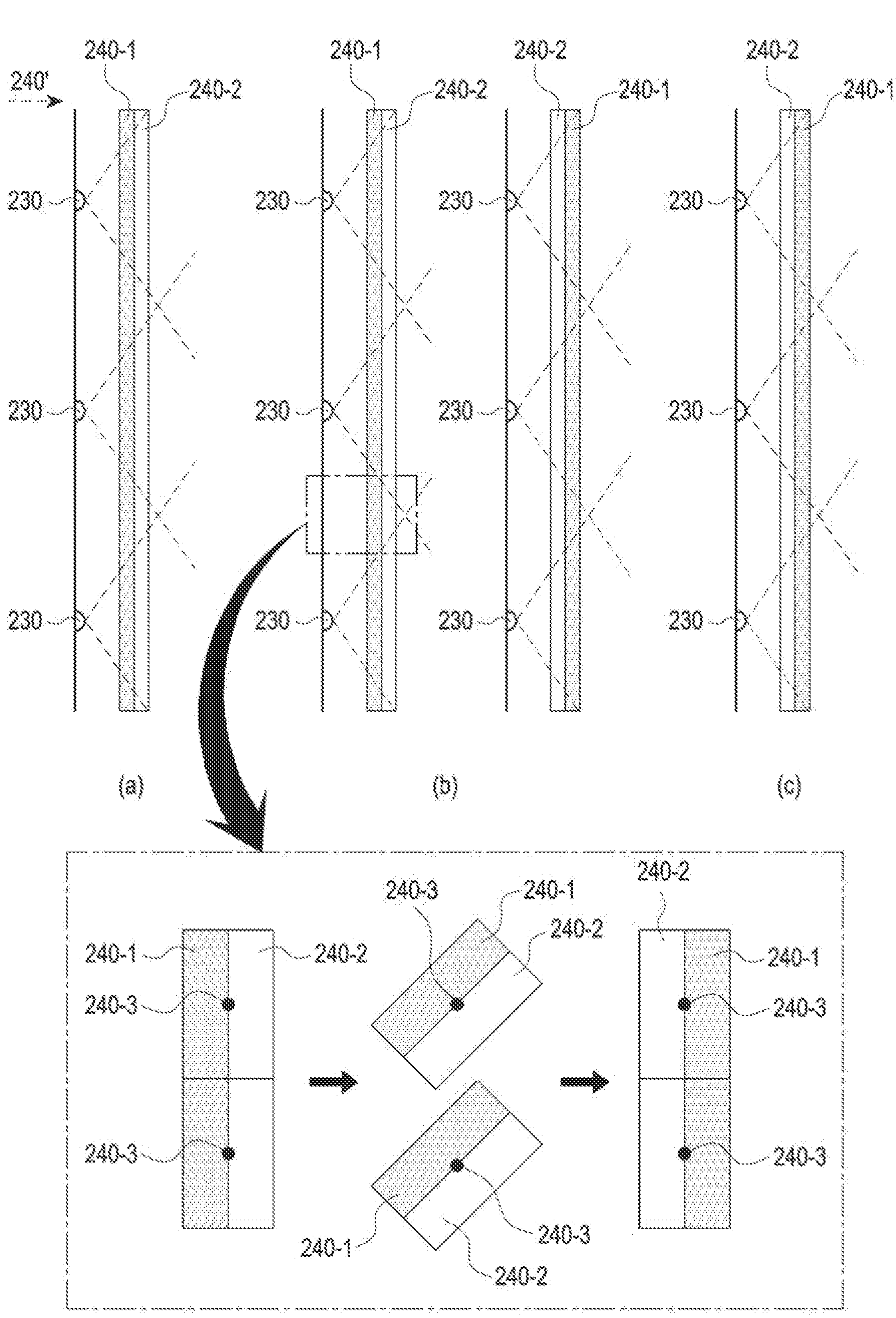
FIG. 19 is a diagram illustrating an example in which a plurality of subfilters included in a photocatalyst filter are switched according to various embodiments of the disclosure.

FIG. 19 is a diagram illustrating an example in which a plurality of subfilters included in a photocatalyst filter are switched according to various embodiments of the disclosure.

Referring to FIG. 19, the photocatalyst filter 240 may include a plurality of separated subfilters. In the enlarged view in (b) of FIG. 19, the photocatalyst filter 240 may include a plurality of subfilters 240' separated in the width direction. According to various embodiments of the disclosure, in the recycling mode of the photocatalyst filter 240, the front section and the rear section of the plurality of subfilters may be switched.

The plurality of subfilters 240' may include a first portion 240-1 positioned toward the first light source 230 from the virtual line passing through the middle area of the filter and a second portion 240-2 facing away from the first portion 240-1. For example, when the air clean mode of the electronic device 10 is terminated or activated, contaminants may remain adsorbed to the beads positioned in the second portion 240-2 of the plurality of subfilters 240'. To remove the contaminants to increase recycling efficiency, the first portion 240-1 and second portion 240-2 of the plurality of subfilters 240' may be switched. According to an embodiment, the plurality of subfilters 240' may be rotated 180 degrees about the axis 240-3 formed in the center of the filter. For example, after first recycling of the photocatalyst filter 240, the first portion 240-1 and the second portion 240-2 of the plurality of subfilters 240' may be switched so that the second portion 240-2 faces the light source 230 while the first portion 240-1 faces away from the light source 230, and then, second recycling of the photocatalyst filter 240 may be performed.

According to the embodiment shown in FIG. 19, it is possible to increase the recycling effect by the effect of mixing the beads 300 in the photocatalyst filter 240.

Figure 20:
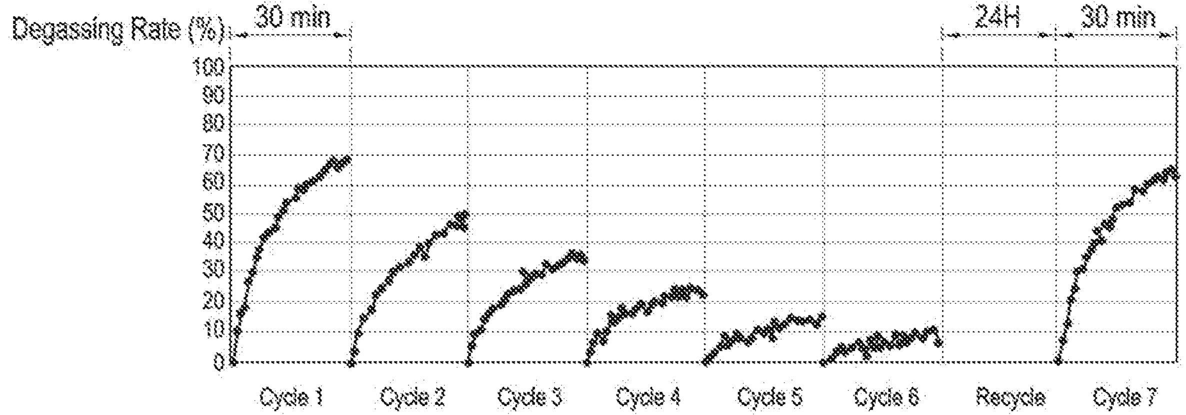
FIG. 20 is a diagram illustrating the degassing efficiency per cycle of a photocatalyst filter according to various embodiments of the disclosure.

FIG. 20 is a diagram illustrating the degassing efficiency per cycle of a photocatalyst filter according to various embodiments of the disclosure.

For example, referring to FIG. 20, according to various embodiments of the disclosure, the degassing rate may be gradually lowered according to the operation cycles of the air purifier when operating the air clean function using the photocatalyst filter 240. If contaminants adsorbed to the beads 300 of the photocatalyst filter 240 are not removed but accumulated, the degassing efficiency may be drastically lowered whenever the air clean function is repeatedly used. Accordingly, the photocatalyst filter 240 according to various embodiments of the disclosure may be recycled after using the air clean function a predetermined number of times. FIG. 20 illustrates an example in which the degassing efficiency of the photocatalyst filter 240 is lowered every cycle of, for example, a period of 30 minutes. It may be identified that the degassing efficiency is recovered to a degree similar to that in the initial state by recycling the photocatalyst filter 240 during or for a predetermined time (e.g., 24 hours) after some cycles, according to various embodiments of the disclosure described above through the embodiments of FIGS. 1 to 19.

By the photocatalyst filter and electronic device according to various embodiments of the disclosure, the air purifying effect and filter recycling effect may be enhanced without increasing the number of light sources and the amount of light, saving manufacturing costs and energy consumption.

By the photocatalyst filter and electronic device according to various embodiments of the disclosure, prevent contaminants from remaining in the blind spots of the photocatalyst filter may be prevented, enhancing the air purifying effect and filter recycling effect.

According to an embodiment, the electronic devices disclosed herein may be configured to provide a flap assembly having a form of a metal foil and that effectively removes contaminants inside the photocatalyst filter, thereby significantly increasing the filter recycling effect without greatly increasing manufacturing costs.

According to various embodiments of the disclosure, hybrid beads including a photocatalyst material may be provided to decompose contaminants on the fluid by causing photocatalyst oxidation and an adsorbent may be provided to adsorb the contaminants on the fluid. According to various embodiments of the disclosure, a hybrid-type air purification device may be provided that addresses the drawbacks of the decomposition type air purification device, which suffers from slow purification, and the adsorption type air purification device, which does not properly remove microorganisms and requires filter replacement.

According to various embodiments of the disclosure, various methods for determining the recycling cycle of the photocatalyst filter are provided, thereby providing the advantage of automatically recycling the photocatalyst filter.

It should be appreciated that various embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

According to various embodiments, each component (e.g., a module or a program) of the above-described components may include a single entity or multiple entities. Some of the plurality of entities may be separately disposed in different components. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

It is apparent to one of ordinary skill in the art that a photocatalyst filter and an electronic device including the same according to various embodiments of the disclosure as described above are not limited to the above-described embodiments and those shown in the drawings, and various changes, modifications, or alterations may be made thereto without departing from the scope of the present disclosure.

What is claimed is:

1. An electronic device comprising:

a housing;

a photocatalyst filter;

a first sensor provided in the housing and configured to measure a quality of air inside the electronic device;

a blower fan configured to introduce air into the housing;

a light source configured to emit light to the photocatalyst filter; and a processor configured to:

control the blower fan and the light source, determine a degree of contamination of air inside the electronic device based on a first sensor value of the first sensor for a predetermined time period;

determine a degree of contamination of air outside the electronic device based on a second sensor value of a second sensor that is provided outside of the housing for the predetermined time period; and recycle the photocatalyst filter based on an amount of increase of the first sensor value being larger than an amount of increase of the second sensor value over the predetermined time period, or based on an amount of decrease of the first sensor value being smaller than an amount of decrease of the second sensor value over the predetermined time period, wherein the first sensor and the second sensor are configured to measure a concentration of a same contaminant in air.

2. The electronic device of claim 1, wherein the photocatalyst filter comprises:

a body having an internal space through which a fluid passes;

a plurality of photocatalyst beads provided in the internal space; and a flap assembly connected with the body and configured to open or close based on a flow of the fluid, and wherein the flap assembly comprises a reflecting plate configured increase an amount of light reaching the plurality of photocatalyst beads by reflecting light when the flap assembly is closed.

3. The electronic device of claim 2, wherein the body comprises a first opening provided on a front surface of the body and a second opening provided on a rear surface of the body, wherein the flap assembly is further configured to open or close over the second opening, and wherein the reflecting plate is on one surface of the is configured to face the first opening when the flap assembly is closed over the second opening.

4. The electronic device of claim 2, wherein the flap assembly is further configured to be opened or closed by the air introduced into the housing by the blower fan.

5. The electronic device of claim 2, wherein the plurality of photocatalyst beads comprises hybrid beads, and wherein the hybrid beads comprise:

a photocatalyst material that decomposes at least some of contaminants in the fluid by causing photocatalytic oxidation; and an adsorbent that absorbs at least some of the contaminants in the fluid.

6. The electronic device of claim 2, wherein the reflecting plate comprises a light scattering material, or a portion provided on a surface thereof and configured to scatter light.

7. The electronic device of claim 1, wherein the housing comprises a flap assembly configured to open or close based on a flow of a fluid, wherein the photocatalyst filter comprises a plurality of photocatalyst beads; and wherein the flap assembly comprises a reflecting plate configured to increase an amount of light reaching the plurality of photocatalyst beads when the flap assembly is closed.

8. The electronic device of claim 1, wherein the processor is further configured to, after an air clean mode of the electronic device is terminated, recycle the photocatalyst filter based on the amount of increase of the first sensor value obtained by the first sensor provided in the housing being larger than the amount of increase of the second sensor value obtained from the second sensor outside the housing.

9. The electronic device of claim 1, wherein the processor is further configured to, while an air clean mode of the electronic device is running, recycle the photocatalyst filter based on the amount of decrease of the first sensor value obtained by the first sensor provided in the housing being smaller than the amount of decrease of the second sensor value obtained from the second sensor outside the housing.

10. The electronic device of claim 8, wherein the photocatalyst filter is recycled based on a recycling time determined by the processor.

11. The electronic device of claim 1, wherein the processor is further configured to increase an amount of light emitted by the light source in a recycling mode of the photocatalyst filter.

12. The electronic device of claim 1, wherein the processor is further configured to increase an intensity of light emitted by the light source in a recycling mode of the photocatalyst filter.

13. The electronic device of claim 1, wherein the processor is further configured to change a light radiation direction of the light source in a recycling mode of the photocatalyst filter.

14. The electronic device of claim 1, wherein the processor is further configured to reverse an air flow direction of the blower fan in a recycling mode of the photocatalyst filter.

15. The electronic device of claim 1, wherein the photocatalyst filter comprises a plurality of subfilters which are separated, and wherein a front section of the plurality of subfilters and a rear section of the plurality of subfilters are switched in a recycling mode of the photocatalyst filter.

* * * * *